(12) United States Patent
Cooper et al.

(10) Patent No.: US 9,290,742 B2
(45) Date of Patent: Mar. 22, 2016

(54) TISSUE ENGINEERED BLOOD VESSEL

(71) Applicant: CORDIS CORPORATION, Bridgewater, NJ (US)

(72) Inventors: Kevin Cooper, Flemington, NJ (US); Iksoo Chun, Princeton, NJ (US); David C. Colter, Hamilton, NJ (US); Sridevi Dhanaraj, Raritan, NJ (US); Anna Gosiewska, Skillman, NJ (US); Agnieszka Seyda, Belle Mead, NJ (US); Carrie H. Fang, Pittstown, NJ (US); Chunlin Yang, Belle Mead, NJ (US)

(73) Assignee: CORDIS CORPORATION, Bridgewater, NJ (US)

( * ) Notice: Subject to any disclaimer, the term of this patent is extended or adjusted under 35 U.S.C. 154(b) by 145 days.

(21) Appl. No.: 13/799,520

(22) Filed: Mar. 13, 2013

(65) Prior Publication Data

US 2013/0196431 A1    Aug. 1, 2013

Related U.S. Application Data

(62) Division of application No. 12/432,994, filed on Apr. 30, 2009, now abandoned.

(60) Provisional application No. 61/049,067, filed on Apr. 30, 2008.

(51) Int. Cl.
| | |
|---|---|
| *C12N 5/00* | (2006.01) |
| *C12N 5/071* | (2010.01) |
| *A61L 27/18* | (2006.01) |
| *A61L 27/36* | (2006.01) |
| *A61L 27/38* | (2006.01) |
| *A61L 27/50* | (2006.01) |

(52) U.S. Cl.
CPC .............. *C12N 5/0691* (2013.01); *A61L 27/18* (2013.01); *A61L 27/3604* (2013.01); *A61L 27/38* (2013.01); *A61L 27/507* (2013.01)

(58) Field of Classification Search
CPC ............. C12N 2533/40; C12N 5/0068; C12N 2533/30; A61F 2/06
See application file for complete search history.

(56) References Cited

U.S. PATENT DOCUMENTS

| | | |
|---|---|---|
| 4,801,299 A | 1/1989 | Brendel et al. |
| 5,676,698 A | 10/1997 | Janzen et al. |
| 5,705,181 A | 1/1998 | Cooper et al. |
| 5,922,024 A | 7/1999 | Janzen et al. |
| 5,951,997 A | 9/1999 | Bezwada et al. |
| 6,113,624 A | 9/2000 | Bezwada et al. |
| 6,293,970 B1 | 9/2001 | Wolfinbarger, Jr. et al. |

(Continued)

FOREIGN PATENT DOCUMENTS

| | | |
|---|---|---|
| DE | 102006058755 A1 | 6/2008 |
| EP | 0610086 A2 | 8/1994 |

(Continued)

OTHER PUBLICATIONS

Kakisis et al., Artificial blood vessel: The Holy Grail of peripheral vascular surgery, J Vasc Surg 2005;41:349-54.*

(Continued)

*Primary Examiner* — Reza Ghafoorian

(57) ABSTRACT

Compositions and methods of using tissue engineered blood vessels to repair and regenerate blood vessels of patients with vascular disease are disclosed.

1 Claim, 16 Drawing Sheets

(56) References Cited

U.S. PATENT DOCUMENTS

| | | | |
|---|---|---|---|
| 6,306,424 | B1 | 10/2001 | Vyakarnam et al. |
| 6,333,029 | B1 | 12/2001 | Vyakarnam et al. |
| 6,355,699 | B1 | 3/2002 | Vyakarnam et al. |
| 6,365,149 | B2 | 4/2002 | Vyakarnam et al. |
| 6,423,252 | B1 | 7/2002 | Chun et al. |
| 6,534,084 | B1 | 3/2003 | Vyakarnam et al. |
| 6,599,323 | B2 | 7/2003 | Melican et al. |
| 6,743,574 | B2 | 6/2004 | Wolfinbarger, Jr. et al. |
| 6,933,326 | B1 | 8/2005 | Griffey et al. |
| 6,942,961 | B1 | 9/2005 | Baumgartner |
| 7,029,689 | B2 | 4/2006 | Berglund et al. |
| 7,112,218 | B2 | 9/2006 | McAllister et al. |
| 7,112,417 | B2 | 9/2006 | Vyakarnam et al. |
| 7,192,604 | B2 | 3/2007 | Brown et al. |
| 7,208,177 | B2 | 4/2007 | Geistlich et al. |
| 7,413,575 | B2 | 8/2008 | Phaneuf et al. |
| 7,470,015 | B2 | 12/2008 | Fukushige |
| 7,510,873 | B2 | 3/2009 | Mistry et al. |
| 7,521,231 | B2 | 4/2009 | Germain et al. |
| 7,622,299 | B2 | 11/2009 | Sanders et al. |
| 7,666,803 | B2 | 2/2010 | Shetty et al. |
| 7,749,204 | B2 | 7/2010 | Dhanaraj et al. |
| 7,763,459 | B2 | 7/2010 | Padmini et al. |
| 7,846,728 | B2 | 12/2010 | Brooks et al. |
| 2003/0100944 | A1 | 5/2003 | Laksin et al. |
| 2003/0171053 | A1 | 9/2003 | Sanders |
| 2003/0211130 | A1 | 11/2003 | Sanders et al. |
| 2004/0076657 | A1 | 4/2004 | Wolfinbarger et al. |
| 2004/0078090 | A1 | 4/2004 | Binette et al. |
| 2005/0113938 | A1 | 5/2005 | Jamiolkowski et al. |
| 2005/0159822 | A1 | 7/2005 | Griffey et al. |
| 2005/0260612 | A1 | 11/2005 | Padmini et al. |
| 2006/0223177 | A1 | 10/2006 | Harris et al. |
| 2006/0293743 | A1 | 12/2006 | Andersen et al. |
| 2007/0038290 | A1 | 2/2007 | Huang et al. |
| 2007/0160588 | A1 | 7/2007 | Kihm |
| 2007/0218099 | A1 | 9/2007 | Kim et al. |
| 2007/0230281 | A1 | 10/2007 | You et al. |
| 2008/0081323 | A1 | 4/2008 | Keeley et al. |
| 2008/0131473 | A1* | 6/2008 | Brown et al. ............ 424/423 |
| 2008/0204855 | A1 | 8/2008 | Yamamoto |
| 2008/0208325 | A1 | 8/2008 | Helmus et al. |
| 2008/0220042 | A1 | 9/2008 | Hashi et al. |
| 2009/0104276 | A1 | 4/2009 | Andjelic et al. |
| 2009/0163990 | A1 | 6/2009 | Yang et al. |
| 2009/0263484 | A1* | 10/2009 | Hammer et al. ........... 424/486 |
| 2009/0264040 | A1 | 10/2009 | Erneta et al. |
| 2009/0275129 | A1 | 11/2009 | Cooper et al. |
| 2010/0047310 | A1 | 2/2010 | Chen et al. |
| 2010/0063539 | A1 | 3/2010 | Yang et al. |
| 2010/0070020 | A1 | 3/2010 | Hashi et al. |
| 2011/0076329 | A1 | 3/2011 | Cook et al. |
| 2011/0106250 | A1 | 5/2011 | Brooks et al. |

FOREIGN PATENT DOCUMENTS

| | | | |
|---|---|---|---|
| EP | 464163 | B1 | 5/1995 |
| EP | 1214952 | A1 | 6/2002 |
| JP | 2007307132 | | 11/2007 |
| WO | WO 99/42528 | A2 | 8/1999 |
| WO | WO 99/44487 | A2 | 9/1999 |
| WO | WO 99/66965 | A1 | 12/1999 |
| WO | WO 2005/003317 | A2 | 1/2005 |
| WO | WO 2006/068972 | A2 | 6/2006 |
| WO | WO 2008/068072 | A1 | 6/2008 |
| WO | WO 2009/134991 | A2 | 11/2009 |
| WO | WO 2010/040129 | A2 | 4/2010 |

OTHER PUBLICATIONS

Boland et la., Electrospinning polydioxanone for biomedical applications, Acta Biomaterialia 1 (2005) 115-123.*

Bhattarai, Shanta Raj et al., "Novel Biodegradable Electrospun Membrane: Scaffold for Tissue Engineering", Biomaterials, 25, 2004, pp. 2595-2602.

Cho, Kwang Jun et al., "Fabrication and Characterization of Hydrophilized Polydioxanon Scaffolds for Tissue Engineering Application", www.scientific.net/requestpaper/52768, Key Engineering Materials, vols. 342-343, 2007, pp. 289-292.

Chung, Sanwon et al., "Bioresorbable Elastomeric Vascular Tissue Engineering Scaffolds Via Melt Spinning and Electrospinning", Acta Biomaterialia, 2010, pp. 1958-1967, vol. 6.

Korossis, S.A. et al., "Bioreactors in Tissue Engineering", Topics in Tissue Engineering, vol. 2, 2005, Chapter 8, pp. 2-23.

Kuroda, M.D., R. et al., "Treatment of a Full-Thickness Articular Cartilage Defect in the Femoral Condyle of an Athlete with Autollous Bone-Marrow Stromal Cells", Osteoarthritis and Cartilage 2007, 226-231.

L'Heureux, Nicolas et al., "A Complete Biological Tissue-Engineered Human Blood Vessel", The FASEB Journal, 1998, 12: pp. 47-56.

L'Heureux, Nicolas et al., "Tissue-Engineered Blood Vessel for Adult Arterial Revascularization", The New England Journal of Medicine, vol. 357, pp. 1451-1453, Oct. 4, 2007.

McAllister, Todd, The First Completely Autologous Tissue-Engineered Vascular Grafts for Dialysis Patients—A Revolutionary Milestone, www.medicalnewstoday.com.

Sachlos, E. et al., "Making Tissue Engineering Scaffolds Work. Review on the Application of Solid Freeform Fabrication Technology to the Production of Tissue Engineering Scaffolds", European Cells and Materials, vol. 5, 2003, pp. 29-40.

Vaz, C.M., "Design of Scaffolds for Blood Vessel Tissue Engineering Using a Multi-Layering Electrospinning Technique", www.ncbi.nlm.nih.gic/pubmed/16701837.

International Search Report dated Jun. 10, 2010 in corresponding International Application No. PCT/US2009/042293.

International Search Report dated Mar. 16, 2012 in corresponding International Application No. PCT/US2011/063852.

International Search Report dated Jan. 16, 2013 in corresponding International Application No. PCT/US2012/059858.

JP Office Action, mailed Jul. 29, 2014, for JP Patent Appln. No. 2011-507640.

* cited by examiner

TISSUE ENGINEERED BLOOD VESSEL

CROSS-REFERENCE TO RELATED APPLICATIONS

This application is a divisional of U.S. application Ser. No. 12/432,994 filed on Apr. 30, 2009, which application claims the benefit under U.S. Provisional Application Ser. No. 61/049,067 filed Apr. 30, 2008, which is hereby incorporated by reference in its entirety.

FIELD OF THE INVENTION

The invention relates to tissue engineered blood vessels for treatment of vascular disease. In particular, the invention provides tissue engineered blood vessels prepared from scaffolds, and one or more of cells, cell sheets, cell lysate, minced tissue, and bioreactor processes to repair or replace a native blood vessel that has been damaged or diseased.

BACKGROUND OF THE INVENTION

Cardiovascular-related disorders are a leading cause of death in developed countries. In the US alone, one cardiovascular death occurs every 34 seconds and cardiovascular disease-related costs are approximately $250 billion. Current methods for treatment of vascular disease include chemotherapeutic regimens, angioplasty, insertion of stents, reconstructive surgery, bypass grafts, resection of affected tissues, or amputation. Unfortunately, for many patients, such interventions show only limited success, and many patients experience a worsening of the conditions or symptoms.

These diseases often require reconstruction and replacement of blood vessels. Currently, the most popular source of replacement vessels is autologous arteries and veins. However, such autologous vessels are in short supply or are not suitable especially in patients who have had vessel disease or previous surgeries.

Synthetic grafts made of materials such, as PTFE and Dacron are popular vascular substitutes. Despite their popularity, synthetic materials are not suitable for small diameter grafts or in areas of low blood flow. Material-related problems such as stenosis, thromboembolization, calcium deposition, and infection have also been demonstrated.

Therefore, there is a clinical need for biocompatible and biodegradable structural matrices that facilitate tissue infiltration to repair/regenerate diseased or damaged tissue. In general, the clinical approaches to repair damaged or diseased blood vessel tissue do not substantially restore their original function. Thus, there remains a strong need for alternative approaches for tissue repair/regeneration that avoid the common problems associated with current clinical approaches.

The emergence of tissue engineering may offer alternative approaches to repair and regenerate damaged/diseased tissue. Tissue engineering strategies have explored the use of biomaterials in combination with cells, growth factors, bioactives and bioreactor processes to develop biological substitutes that ultimately can restore or improve tissue function. The use of colonizable and remodelable scaffolding materials has been studied extensively as tissue templates, conduits, barriers, and reservoirs. In particular, synthetic and natural materials in the form of foams, and textiles have been used in vitro and in vivo to reconstruct/regenerate biological tissue, as well as deliver agents for inducing tissue growth.

Such tissue-engineered blood vessels (TEBVs) have been successfully fabricated in vitro and have been used in animal models. However, there has been very limited clinical success.

Regardless of the composition of the scaffold and the targeted tissue, the template must possess some fundamental characteristics. The scaffold must be biocompatible, possess sufficient mechanical properties to resist the physical forces applied at the time of surgery, porous enough to allow cell invasion, or growth, easily sterilized, able to be remodeled by invading tissue, and degradable as the new tissue is being formed. Furthermore, the scaffold may be fixed to the surrounding tissue via mechanical means, fixation devices, or adhesives. So far, conventional materials, alone or in combination, lack one or more of the above criteria. Accordingly, there is a need for scaffolds that can resolve the potential pitfalls of conventional materials.

SUMMARY OF THE INVENTION

The invention is a tissue engineered blood vessel (TEBV) comprised of a biocompatible, bioabsorbable scaffold and one or more of cells, cell sheets, cell lysate, minced tissue, and cultured with or without a bioreactor process. Such tissue engineered blood vessels may be used to repair or replace a native blood vessel that has been damaged or diseased. In one embodiment, the tissue engineered blood vessel is comprised of a biocompatible, bioabsorbable scaffold and cells. In another embodiment the tissue engineered blood vessel is comprised of a biocompatible, bioabsorbable scaffold and cell sheets. In another embodiment the tissue engineered blood vessel is comprised of a biocompatible, bioabsorbable scaffold and cell lysate. In yet another embodiment the tissue engineered blood vessel is comprised of a biocompatible, bioabsorbable scaffold and minced tissue. In addition, various combinations of cells, cell sheets, cell lysate and minced tissue are combined with a biocompatible, bioabsorbable scaffold to form the tissue engineered bloods vessel. These tissue engineered blood vessels may be cultured with or without a bioreactor process. In one embodiment, the tissue engineered blood vessel is enhanced by combining with bioactive agents.

DETAILED DESCRIPTION OF INVENTION

Figure 1:
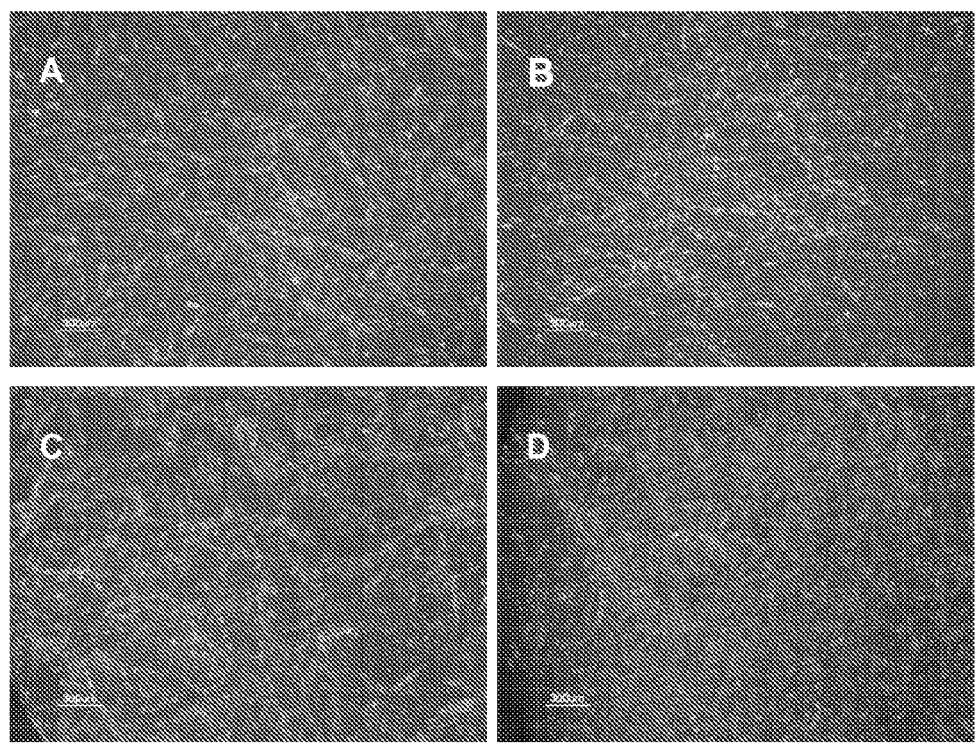
FIG. 1. Human umbilical cord-derived cell (hUTC) attachment and growth on a vascular graft biomaterial after 3 and 7 days in culture. A: PDO-ESS scaffold after 3 days, B: PDO-ESS scaffold after 7 days, C: PDO/collagen-ESS scaffold after 3 days, D: PDO/collagen-ESS scaffold after 7 days. All images taken at 40× magnification FIG. 2. Representative example of smooth muscle cell (UASMC) cell attachment and growth on a vascular graft biomaterial after 3 and 7 days in culture. A: 100 mg/ml PDO-ESS scaffold after 3 days, B: 100 mg/ml PDO-ESS scaffold after 7 days, C: 140 mg/ml PDO-ESS scaffold after 3 days, D: 140 mg/ml PDO-ESS scaffold after 7 days. All images taken at 40× magnification.

The invention is a tissue engineered blood vessel (TEBV) comprised of a biocompatible, bioabsorbable scaffold and one or more of cells, cell sheets, cell lysate, minced tissue, and cultured with or without a bioreactor process. Such tissue engineered blood vessels may be used to repair or replace a native blood vessel that has been damaged or diseased. In tissue engineering, the rate of resorption of the scaffold by the body preferably approximates the rate of replacement of the scaffold by tissue. That is to say, the rate of resorption of the scaffold relative to the rate of replacement of the scaffold by tissue must be such that the structural integrity, e.g. strength, required of the scaffold is maintained for the required period of time. If the scaffold degrades and is absorbed unacceptably faster than the scaffold is replaced by tissue growing therein, the scaffold may exhibit a loss of strength and failure of the device may occur. Additional surgery then may be required to remove the failed scaffold and to repair damaged tissue. Thus, devices of the present invention advantageously balance the properties of biodegradability, resorption, structural integrity over time and the ability to facilitate tissue in-growth, each of which is desirable, useful or necessary in tissue regeneration or repair. Such devices provide synergistic improvements over devices of the prior art.

In general, a suitable biodegradable polymer for preparing the scaffold is desirably configured so that it has mechanical properties that are suitable for the intended application, remains sufficiently intact until tissue has in-grown and healed, does not invoke a minimal inflammatory response or toxic response, is capable of withstanding long-term hemodynamic stress without material failure, resistant to both thrombosis and infection and is metabolized in the body after fulfilling its purpose, is easily processed into the desired final product to be formed, demonstrates acceptable shelf-life, and is easily sterilized.

The biocompatible, biodegradable scaffold may be comprised of natural, modified natural or synthetic biodegradable polymers, including homopolymers, copolymers and block polymers, linear or branched, segmented or random; as well as combinations thereof. Particularly well suited synthetic biodegradable polymers are aliphatic polyesters which include but are not limited to homopolymers and copolymers of lactide (which includes lactic acid D-, L- and meso lactide), glycolide (including glycolic acid), epsilon-caprolactone, p-dioxanone (1,4-dioxan-2-one), and trimethylene carbonate (1,3-dioxan-2-one). In one embodiment the polymers are poly(p-dioxanone), poly(lactide-co-glycolide) (PLA/PGA) copolymers (95/5, 85/15, 10/90 mole-mole %), and poly(glycolide-co-caprolactone) (PGA/PCL) 65/35 copolymers, and poly(lactide-co-caprolactone) (PLA/PCL) (60/40 mole-mole %) copolymers.

Suitable natural polymers include, but are not limited to collagen, atelocollagen, elastic, and fibrin and combinations thereof. In one embodiment, the natural polymer is collagen. In yet another embodiment, the combination of natural polymer is a acellular omental matrix.

The scaffold has dimensions that reflect desired ranges that, in combination with the one or more of cells, cell sheets, cell lysate, minced tissue, and a bioreactor process will replace a small diameter, damaged or diseased vein or artery blood vessel. Desirable dimensions include but are not limited to: internal diameter (3-7 mm preferable, 4-6 mm most preferable); wall thickness (0.1-1 mm preferable, 0.2-0.7 mm most preferable); and length (1-20 cm preferable, 2-10 cm most preferable). The table below shows how the properties of our PDO construct align with those of a natural vessel.

|  | Dimensions | | | Physical Properties | | | |
| --- | --- | --- | --- | --- | --- | --- | --- |
|  | ID (mm) | Wall Thickness (mm) | Length (cm) | Compliance (%) | Burst Pressure (mmHg) | Suture retention (gmf) | Tensile (peak stress) |
| PDO | 2 & 5 | 0.5 | 1-20 | 0.5-1 | 1500-2500 | 310 | 5 MPa |
| Vessel | 2 & 5 | 0.5-0.7 | 1-20 | 0.2-10 | 1500-4500 | 100-500 | 2-20 MPa |

The scaffold has physical properties that reflect desired ranges that, in conjunction with one or more of cells, cell sheets, cell lysate, minced tissue tissue, and a bioreactor process will replace a small diameter, damaged or diseased vein or artery blood vessel. Desirable physical properties include but are not limited to: compliance (0.2-10% preferable, 0.7-7% most preferable); suture retention strength (100 gm-4 Kg preferable, 100-300 gm most preferable); burst strength/pressure (1000-4500 mm Hg preferable, 1500-4500 mm Hg most preferable with greater than 100 mmHg during the bioreactor process); kink resistance (resist kinking during handling during all stages of process-cell seeding, bioreactor, implantation, life of patient); and in-vitro strength retention (1 day-1 yr maintain enough strength until cell and ECM growth overcomes physical property losses of scaffold; 1 day-3 mos under bioreactor "flow" conditions preferable). The scaffold should also have desirable tensile properties (radial and axial) that include but are not limited to: elastic modulus (MPa) of longitudinal/axial (1-200 preferable; 5-100 most preferable) and orthogonal/radial (0.1-100 preferable, 0.5-50 most preferable) and random (0.1-100 preferable, 0.5-50 most preferable) and wet/longitudinal (5-100 preferable, 25-75 preferable); a peak stress (MPa) of longitudinal/axial (1-30 preferable; 2-20 most preferable) and orthogonal/radial (0.5-15 n preferable, 1-10 most preferable) and random (0.5-15 preferable, 1-10 most preferable) and wet/long (1-30 preferable; 2-20 most preferable); failure strain (%) of longitudinal/axial (1-200 preferable; 5-75 most preferable) and orthogonal/radial (5-400 preferable, 10-300 most preferable) and random (5-400 preferable, 10-300 most preferable) and wet/long (1-200 preferable; 20-100 most preferable).

The scaffold has morphology that reflects desired ranges that, in conjunction with one or more of cells, cell sheets, cell lysate, minced tissue, and a bioreactor process will replace a small diameter, damaged or diseased vein or artery blood vessel. Desirable morphology includes but is not limited to: pore size (1-200 um preferable, most preferable less than 100 um); porosity (40-98% preferable, most preferable 60-95%); surface area/vol (0.1-7 $m^2/cm^3$ preferable, most preferable 0.3-5.5 $m^2/cm^3$); water permeability (1-10 ml $cm^2$/min #80-120 mmHg preferable, most preferable <5 ml $cm^2$/min #120 mmHg); and orientation of polymer/fibers (allows proper cell seeding, adherence, growth, and ECM formation). Polymer/fiber orientation will also allow proper cell migration; also important for the minced tissue fragments such that cells will migrate out of the fragments and populate the scaffold.

The scaffold has biocompatibility that reflects desired properties for a scaffold that, in conjunction with one or more of cells, cell sheets, cell lysate, minced tissue and a bioreactor process will replace a small diameter, damaged or diseased vein or artery blood vessel. Desirable biocompatibility includes but is not limited to: absorption (1 wk-4 yrs preferable, most preferable 4 wks-30 wks to allow greatest vol of scaffold to be occupied by cells and ECM); tissue reaction (minimal); cell compatibility (adherence, viability, growth, migration and differentiation not negatively impacted by scaffold); residual solvent (minimal); residual EtO (minimal); and hemocompatible (non-thrombogenic).

The scaffold has other factors that reflect desired properties for a scaffold that, in conjunction with one or more of cells, cell sheets, cell lysate, minced tissue, tissue and a bioreactor process will replace a small diameter, damaged or diseased vein or artery blood vessel. Desirable factors includes but are not limited to: surface energy (allows proper cell seeding, adherence, growth, migration and ECM formation); surface chemistry (addition of factors such as oxygen, surface roughness or topography (can be utilized to affect cell attachment and other cell functions), nanoscale features on the surface preferably in a size range of 10-1200 nanometers; more preferably 25-900 nanometers (allow preferential endothelial cell attachment), NO, free-radical scavengers allows proper cell seeding, adherence, growth, and ECM formation); cell mediators (addition of factors such as matrix proteins allows proper cell seeding, adherence, growth, migration and ECM formation); hydrophobicity/hydrophilicity (proper balance of hydrophobicity/hydrophilicity allows proper cell seeding, adherence, growth, and ECM formation). Other surface modifications include providing electrical microcurrent in a form of coating a surface with galvanic materials. In particular, zinc and copper (0.01 microns-0.1 microns) can act as an electrical current source enhancing endothelial and smooth muscle cell attachment and proliferation.

Non-limiting examples of a scaffold that may be used in the present invention include textile structures such as felts, weaves, knits, braids, meshes, non-wovens, warped knits; foams, including porous foams and semi-porous foams; perforated films or sheets; patterned films or sheets or fibers; and combinations thereof. As used herein, the term "nonwoven fabric" includes, but is not limited to, bonded fabrics, formed fabrics, or engineered fabrics, that are manufactured by processes other than spinning, weaving or knitting. More specifically, the term "nonwoven fabric" refers to a porous, textile-like material, usually in flat sheet form, composed primarily or entirely of staple fibers assembled in a web, sheet or batt. The fiber diameter is preferably 10 nm to 100 um and more preferably 25 nm to 10 um. In one embodiment, the scaffold is a textile, a foam and combinations thereof.

In another embodiment, the scaffold is a textile comprised of fibers prepared by electrostatic spinning, extrusion, injection molding, as well as any pre- or post-processes (ex. laser cutting to form pours in extruded tube). In one embodiment, the scaffold is a textile prepared by electrostatic spinning. In the electrostatically spun scaffold process, an electrical force is applied to the polymeric solution that overcomes the surface tension of the solution, forming a charged jet. This jet of solution is ejected, dried and solidified onto a substrate to form a sheet, tube or other construct comprised of the electrostatically spun fibers. Spinnability of the polymeric solution is controlled by several parameters that include but are not limited to: concentration (a concentration that allows polymer/solvent solution to be spun and yield fibers that form a proper scaffold (1-50 w/v % preferable); solvent (a solvent that dissolves the polymer in the given concentration range, HFIP preferable); solution viscosity (10-300 mg/ml preferable, 25-250 mg/ml most preferable (50-3000 centipoise)). By controlling the spinning conditions, the resulting fibers can range from about 0.1 µm to about 10 µm and preferably will range from about 0.3 µm to about 5.0 µm.

Other processing parameters for electrostatic spinning that are important include but are not limited to: voltage potential (10-100 kV preferable, most preferable 15-30 kV); flow rate (0.1-20 ml/hr preferable, 1-15 ml/hr most preferable); gap/tip distance (1-35 cm preferable, 2.5-25 cm most preferable); rotation/mandrel rate/speed (10-5,000 rpm preferable, 50-3000 rpm most preferable). The fibers can also be spun from the melt.

Optionally, the strength of the electrostatically spun scaffold (ESSC) may be improved by bonding the fibers of the aforementioned construct. Bonding of the fibers may be accomplished by coating the ESSC with a low melting materials such as PCL and low molecular PLGA copolymers. After coating the scaffold, a post process using a heat press may be performed. The process melts the coated layer on the reinforcement fibers. The molten coating between the electrospun fibers is compressed and fuses the fibers together upon cooling to room temperature. Alternatively, during the electrospinning process, electrospun fibers are exposed with the vapor of the solvent. Upon curing, the fibers fuse together thereby strengthening the scaffold.

In one embodiment the textiles and ESSC scaffolds are prepared from polymers including, but not limited to are poly(p-dioxanone), poly(lactide-co-glycolide) (PLA/PGA) copolymers (95/5, 85/15, 10/90 mole-mole %), and collagen.

In another embodiment the scaffold is a foam. In one embodiment, the foam scaffolds are prepared from elastomeric copolymers. Suitable bioabsorbable, biocompatible elastomeric copolymers include but are not limited to copolymers of epsilon-caprolactone and glycolide (preferably having a mole ratio of epsilon-caprolactone to glycolide of from about 30:70 to about 70:30, preferably 35:65 to about 65:35, and more preferably 45:55 to 35:65); elastomeric copolymers of epsilon-caprolactone and lactide, including L-lactide, D-lactide blends thereof or lactic acid copolymers (preferably having a mole ratio of epsilon-caprolactone to lactide of from about 35:65 to about 65:35 and more preferably 45:55 to 30:70;) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40); elastomeric copolymers of epsilon-caprolactone and p-dioxanone (preferably having a mole ratio of epsilon-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. In one embodiment, the elastomeric copolymer is poly(glycolide-co-caprolatone) (PGA/PCL) 65/35 copolymer or a poly(lactide-co-caprolatone) (PLA/PCL) (60/–40 mole-mole %) copolymer.

Foam scaffolds may be prepared by conventional processes such as, lyophilization, supercritical solvent foaming (i.e., as described in EP 464,163 B1), gas injection extrusion, gas injection molding or casting with an extractable material In one embodiment, the foams are prepared by lyophilization. Suitable methods for lyophilizing elastomeric polymers such as 65/35 PGA/PCL to form foams is described in the examples of U.S. Pat. No. 6,355,699, "Process for Manufacturing Biomedical Foams", assigned to Ethicon, Inc incorporated herein by reference in its entirety.

In another embodiment, leachables can be introduced into the scaffold as an additional method to form pores. Suitable leachable solids include nontoxic leachable materials such as salts (e.g., sodium chloride, potassium chloride, calcium chloride, sodium tartrate, sodium citrate, and the like), biocompatible mono and disaccharides (e.g., glucose, fructose, dextrose, maltose, lactose and sucrose), polysaccharides (e.g., starch, alginate, chitosan), water soluble proteins (e.g., gelatin and agarose).

The foams have microstructures suitable for tissue engineering. The features of such foams can be controlled to suit a desired application by choosing the appropriate conditions to form the foam during lyophilization. These features in absorbable polymers have distinct advantages over the prior art where the scaffolds are typically isotropic or random structures. However, it is preferred that foams used in tissue engineering (i.e. repair or regeneration) have a structure that provides organization at the microstructural level that provides a template that facilitates cellular organization and regeneration of tissue that has the anatomical, biomechanical, and biochemical features of normal tissues. These foams can be used to repair or regenerate tissue (including organs) in animals such as domestic animals, primates and humans.

The features of such foams can be controlled to suit desired application by selecting the appropriate conditions for lyophilization to obtain one or more of the following properties: (1) interconnecting pores of sizes ranging from about 10 to about 200 µm (or greater) that provide pathways for cellular ingrowth and nutrient diffusion; (2) a variety of porosities ranging from about 20% to about 98% and preferably ranging from about 50% to about 95%; (3) gradient in the pore size across one direction for preferential cell culturing; (4) channels that run through the foam for improved cell invasion, vascularization and nutrient diffusion (5) micro-patterning of pores on the surface for cellular organization; (6) tailorability of pore shape and/or orientation (e.g. substantially spherical, ellipsoidal, columnar); (7) anisotropic mechanical properties; (8) composite foams with a polymer composition gradient to elicit or take advantage of different cell response to different materials; (9) blends of different polymer compositions to create structures that have portions that will break down at different rates; (10) foams co-lyophilized or coated with pharmaceutically active compounds; (11) and the ability to make 3 dimensional shapes and devices with preferred microstructures. The inner, or luminal, layer of the scaffold may be optimized for endothelialization through control of the porosity of the surface and the possible addition of a surface treatment. The outermost, or adventitial, layer of the scaffold may be tailored to support smooth muscle cell growth, again by optimizing the porosity (percent porosity, pore size, pore shape and pore size distribution) and by incorporating bioactive factors, pharmaceutical agents, or cells. There may or may not be a barrier layer with low porosity disposed between these two porous layers to increase strength and decrease leakage. Such structural features of the scaffold described herein can also be found in textiles such as, electrostatically spun scaffolds and other scaffolds described herein.

In one embodiment, the scaffold is a combination of foams and textiles. Textiles include woven, knitted, warped knitted (i.e., lace-like), non-woven, and braided structures that act as a reinforcement for the scaffold. The reinforcement should have a sufficient density to permit suturing, but the density should not be so great as to impede proper bonding between the foam and the textile. The reinforcing material may also be formed from a thin, perforation-containing elastomeric sheet with perforations to allow tissue ingrowth.

For example, the present invention also provides a composite scaffold comprising a first layer that is a textile layer and a second layer of biocompatible foam or ESSC. This composite structure allows for the creation of structures with unique mechanical properties. In one embodiment the textile layer could allow the use of sutures, staples or various fixation devices to hold the composite in place. Generally, the textile has a thickness in the range of about 1 micron to 500 microns. The textile layer allows the composite to have variable mechanical strength depending on the design, a different bioabsorption profile, and a different microenvironment for cell invasion and seeding, which are advantageous in a variety of medical applications. The textile layer may be made from a variety of biocompatible polymers and blends of biocompatible polymers, which are preferably bioabsorbable. The biocompatible foam or ESSC may be either contain gradients or channels. The gradient structure has a substantially continuous transition in at least one characteristic selected from the group consisting of composition, stiffness, flexibility, bioabsorption rate, pore architecture and/or microstructure. The gradient structure can be made from a blend of absorbable polymers that form compositional gradient transitions from one polymeric material to a second polymeric material. In situations where a single chemical composition is sufficient for the application, the invention provides a composite that may have microstructural variations in the structure across one or more dimensions that may mimic the anatomical features of the tissue. The channeled structure provides channels that extend through the foam to facilitate cell migration and nutrient flow throughout the channeled structure.

In another embodiment the foam or ESSC may have a textile fused to the top or bottom surface. This way, surface properties of the structure can be controlled such as porosity, permeability, degradation rate and mechanical properties. The textile can be produced via conventional techniques, described herein, and in which a textile can be built up on a lyophilized foam surface. The textile can be produced via an electrostatic spinning process in which a ESSC can be built up on a lyophilized foam surface.

The scaffold may include one or more layers of each of the foam or ESSC and reinforcement components. Preferably, adjacent layers of foam or ESSC are also integrated by at least a partial interlocking of the pore-forming webs or walls in the adjacent layers.

In one embodiment the scaffold may be coated with natural polymers to enhance cellular compatibility. Suitable natural polymers include, but are not limited to collagen, atelocollagen, elastin, hyaluronic acid and fibrin and combinations thereof. In one embodiment, the natural polymer is collagen. In yet another embodiment, the combination of natural polymer is acellular omental matrix.

In one embodiment, the tissue engineered blood vessel is comprised of a biocompatible, bioabsorbable scaffold and cells. The scaffold is as described herein above. Suitable cells that may be combined with the scaffold include, but are not limited to, stem cells such as multipotent or pluripotent stem cells; progenitor cells, such as smooth muscle progenitor cells and vascular endothelium progenitor cells; embryonic stem cells; postpartum tissue derived cells such as, placental tissue derived cells and umbilical tissue derived cells, endothelial cells, such as vascular endothelial cells; smooth muscle cells, such as vascular smooth muscle cells; precursor cells derived from adipose tissue; and arterial cells such as, cells derived from the radial artery and the left and right internal mammary artery (IMA), also known as the internal thoracic artery.

In one embodiment, the TEBV comprises a scaffold as described herein above and human umbilical tissue derived cells (hUTCs). The methods for isolating and collecting human umbilical tissue-derived cells (hUTCs) (also referred to as umbilical-derived cells (UDCs)) are described in copending U.S. application Ser. No. 10/877,012 incorporated herein by reference in its entirety. In another embodiment, the TEBV comprises a scaffold as described herein above, human umbilical tissue derived cells (hUTCs) and one or more other cells. The one or more other cells includes, but is not limited to vascular smooth muscle cells (SMCs), vascular smooth muscle progenitor cells, vascular endothelial cells (ECs), or vascular endothelium progenitor cells, and/or other multipotent or pluripotent stem cells. hUTCs in combination with one or more other cells on the scaffold may enhance the seeding, attachment, and proliferation of for example ECs and SMCs on the scaffold. hUTCS may also promote the differentiation of the EC or SMC or progenitor cells in the scaffold construct. This may promote the maturation of TEBVs during the in vitro culture as well as the engraftment during the in vivo implantation. hUTCs may provide trophic support, or provide and enhance the expression of ECM proteins. The trophic effects of the cells, including hUTCs, can lead to proliferation of the vascular smooth muscle or vascular endothelium of the patient. The trophic effects of the cells, including hUTCs, may induce migration of vascular smooth muscle cells, vascular endothelial cells, skeletal muscle progenitor cells, vascular smooth muscle progenitor cells, or vascular endothelium progenitor cells to the site or sites of the regenerated blood vessel.

Cells can be harvested from a patient (before or during surgery to repair the tissue) and the cells can be processed under sterile conditions to provide a specific cell type. One of skill in the art is aware of conventional methods for harvesting and providing the cells as describe above such as described in Osteoarthritis Cartilage 2007 February; 15(2):226-31 and incorporated herein by reference in their entirety.

The cells can be seeded on the scaffolds of the present invention for a short period of time, e.g. less than one day, just prior to implantation, or cultured for longer a period, e.g. greater than one day, to allow for cell proliferation and extracellular matrix synthesis within the seeded scaffold prior to implantation. In one embodiment, a single cell type is seeded on the scaffold. In another embodiment, one or more cell types are seeded on the scaffold. Various cellular strategies could be used with these scaffolds (i.e., autologous, allogenic, xenogeneic cells etc.).

In another embodiment the cells are genetically modified to express genes of interest responsible for pro-angiogenic activity, anti-inflammatory activity, cell survival, cell proliferation or differentiation or immunemodulation.

In another embodiment the tissue engineered blood vessel is comprised of a biocompatible, bioabsorbable scaffold and cell sheets. Cell sheets may be made of hUTCs or other cell types. Methods of making cell sheets are as described in copending U.S. application Ser. No. 11/304,091 incorporated herein by reference in its entirety. The cell sheet is generated using thermoresponsive polymer coated dishes that allow harvesting intact cell sheets with the decrease of the temperature. Alternatively, other methods of making cell sheets include, but are not limited to growing cells in a form of cell sheets on a polymer film. Selected cells may be cultured on a surface of glass, ceramic or a surface-treated synthetic polymer. For example, polystyrene that has been subjected to a surface treatment, like gamma-ray irradiation or silicon coating, may be used as a surface for cell culture. Cells grown to over 85% confluence form cell sheet layer on cell growth support device. Cell sheet layer may be separated from cell growth support device using proteolysis enzymes, such as trypsin or dispase. Non-enzymatic cell dissociation could also be used. A non-limiting example includes a mixture of chelators sold under the trade name CELLSTRIPPER (Mediatech, Inc., Herndon, Va.), a non-enzymatic cell dissociation solution designed to gently dislodge adherent cells in culture while reducing the risk of damage associated with enzymatic treatments.

Alternatively, the surface of the cell growth support device, from which cultured cells are collected, may be a bed made of a material from which cells detach without a proteolysis enzyme or chemical material. The bed material may comprise a support and a coating thereon, wherein the coating is formed from a polymer or copolymer which has a critical solution temperature to water within the range of 0° C. to 80° C.

In one embodiment, one or more cells sheets are combined with the scaffold as described herein above by wrapping the cell sheet or sheets around the scaffold. The one or more cell sheets may be of the same cell type or of different cell types as described herein above. In one embodiment, multiple cell sheets could be combined to form a robust vascular construct. For example, cell sheets made of endothelial cells and smooth muscle cells could be combined with the scaffold to form TEBVs. Alternatively, other cell types such as hUTC cell sheets could be combined with endothelial cell sheets and the scaffold to form TEBV. Furthermore, cell sheets made of hUTCs can be wrapped around a pre-formed TEBV composed of a scaffold, ECs, and SMCs to provide trophic factors supporting maturation of the construct.

Cell sheets may be grown on the scaffold to provide reinforcement and mechanical properties to the cell sheets. Reinforced cell sheets can be formed by placing biodegradable or non-biodegradable reinforcing members at the bottom of support device prior to seeding support device with cells. Reinforcing members are as described herein above. Cell sheet layer that results will have incorporated the reinforcing scaffold providing additional strength to cell sheet layer, which can be manipulated without the requirement for a backing layer. A preferred reinforcing scaffold is a mesh comprised of poly(dioxanone). The mesh can be placed at the bottom of a Corning® Ultra low attachment dish. Cells can then be seeded on to the dishes such that they will form cell-cell interactions but also bind to the mesh when they interact with the mesh. This will give rise to reinforced cell sheets with better strength and handling characteristics. Such reinforced cell sheets may be rolled into TEBV or the reinforced cell sheet layer may be disposed on a scaffold (as described above).

In another embodiment, the cell sheet is genetically engineered. The genetically engineered cell sheet comprises a population of cells wherein at least one cell of the population of cells is transfected with an exogenous polynucleotide such that the exogenous polynucleotide expresses express diagnostic and/or therapeutic product (e.g., a polypeptide or polynucleotide) to assist in tissue healing, replacement, maintenance and diagnosis. Examples of "proteins of interest" (and the genes encoding same) that may be employed herein include, without limitation, cytokines, growth factors, chemokines, chemotactic peptides, tissue inhibitors of metalloproteinases, hormones, angiogenesis modulators either stimulatory or inhibitory, immune modulatory proteins, neuroprotective and neuroregenerative proteins and apoptosis inhibitors. More specifically, preferred proteins include, without limitation, erythropoietin (EPO), EGF, VEGF, FGF, PDGF, IGF, KGF, IFN-α, IFN-δ, MSH, TGF-α, TGF-β, TNF-α, IL-1, BDNF, GDF-5, BMP-7 and IL-6.

In another embodiment the tissue engineered blood vessel is comprised of a biocompatible, bioabsorbable scaffold and cell lysate. Cell lysates may be obtained from cells including, but not limited to stem cells such as multipotent or pluripotent stem cells; progenitor cells, such as smooth muscle progenitor cells and vascular endothelium progenitor cells; embryonic stem cells; postpartum tissue derived cells such as, placental tissue derived cells and umbilical tissue derived cells, endothelial cells, such as vascular endothelial cells; smooth muscle cells, such as vascular smooth muscle cells; precursor cells derived from adipose tissue; and arterial cells such as, cells derived from the radial artery and the left and right internal mammary artery (IMA), also known as the internal thoracic artery. The cell lysates and cell soluble fractions may be stimulated to differentiate along a vascular smooth muscle or vascular endothelium pathway. Such lysates and fractions thereof have many utilities. Use of lysate soluble fractions (i.e., substantially free of membranes) in vivo, for example, allows the beneficial intracellular milieu to be used allogeneically in a patient without introducing an appreciable amount of the cell surface proteins most likely to trigger rejection, or other adverse immunological responses. Methods of lysing cells are well-known in the art and include various means of mechanical disruption, enzymatic disruption, or chemical disruption, or combinations thereof. Such cell lysates may be prepared from cells directly in their growth medium and thus containing secreted growth factors and the like, or may be prepared from cells washed free of medium in, for example, PBS or other solution.

In yet another embodiment the tissue engineered blood vessel is comprised of a biocompatible, bioabsorbable scaffold and minced tissue. Minced tissue has at least one viable cell that can migrate from the tissue fragments onto the scaffold. More preferably, the minced tissue contains an effective amount of cells that can migrate from the tissue fragments and begin populating the scaffold. Minced tissue may be obtained from one or more tissue sources or may be obtained from one source. Minced tissue sources include, but are not limited to muscle tissue, such as skeletal muscle tissue and smooth muscle tissue; vascular tissue, such as venous tissue and arterial tissue; skin tissue, such as endothelial tissue; and fat tissue.

The minced tissue is prepared by first obtaining a tissue sample from a donor (autologous, allogeneic, or xenogeneic) using appropriate harvesting tools. The tissue sample is then finely minced and divided into small fragments either as the tissue is collected, or alternatively, the tissue sample can be minced after it is harvested and collected outside the body. In embodiments where the tissue sample is minced after it is harvested, the tissue samples can be washed three times in phosphate buffered saline. The tissue can then be minced into small fragments in the presence of a small quantity, for example, about 1 ml, of a physiological buffering solution, such as, phosphate buffered saline, or a matrix digesting enzyme, such as 0.2% collagenase in Ham's F12 medium. The tissue is minced into fragments of approximately 0.1 to 1 mm$^3$ in size. Mincing the tissue can be accomplished by a variety of methods. In one embodiment, the mincing is accomplished with two sterile scalpels cutting in parallel and opposing directions, and in another embodiment, the tissue can be minced by a processing tool that automatically divides the tissue into particles of a desired size. In one embodiment, the minced tissue can be separated from the physiological fluid and concentrated using any of a variety of methods known to those having ordinary skill in the art, such as for example, sieving, sedimenting or centrifuging. In embodiments where the minced tissue is filtered and concentrated, the suspension of minced tissue preferably retains a small quantity of fluid in the suspension to prevent the tissue from drying out.

The suspension of minced living tissue can be used to create a TEBV according to the present invention by depositing the suspension of living tissue upon a biocompatible scaffold, such that the tissue and the scaffold become associated. Preferably, the tissue is associated with at least a portion of the scaffold. The TEBV can be implanted in a subject immediately, or alternatively, the construct can be incubated under sterile conditions that are effective to maintain the viability of the tissue sample.

In another aspect of the invention, the minced tissue could consist of the application of two distinct minced tissue sources (e.g., one surface could be loaded with minced endothelial tissue and the other surface could be loaded with mince smooth muscle tissue).

In one embodiment, the tissue engineered blood vessels comprising a scaffold and one or more of cells, cell sheets, cell lysate, or minced tissue is enhanced by combining with bioactive agents. Suitable bioactive agents include, but are not limited to an antithrombogenic agent, an anti-inflammatory agent, an immunosuppressive agent, an immunomodulatory agent, pro-angiogenic, an antiapoptotic agent, antioxidants, growth factors, angiogenic factors, myoregenerative or myoprotective drugs, conditioned medium, extracellular matrix proteins, such as, collagen, atelocollagen, laminin, fibronectin, vitronectin, tenascin, integrins, glycosaminoglycans (hyaluronic acid, chondroitin sulfate, dermatan sulfate, heparan sulfate, heparin, keratan sulfate and the like), elastin and fibrin; growth factors and/or cytokines, such as vascular endothelial cell growth factors, platelet derived growth factors, epidermal growth factors, fibroblast growth factors, hepatocyte growth factors, insulin-like growth factors, and transforming growth factors.

Conditioned medium from cells as described previously herein allows the beneficial trophic factors secreted by the cells to be used allogeneically in a patient without introducing intact cells that could trigger rejection, or other adverse immunological responses. Conditioned medium is prepared by culturing cells in a culture medium, then removing the cells from the medium. Conditioned medium prepared from populations of cells, including hUTCs, may be used as is, further concentrated, for example, by ultrafiltration or lyophilization, or even dried, partially purified, combined with pharmaceutically-acceptable carriers or diluents as are known in the art, or combined with other bioactive agents Conditioned medium may be used in vitro or in vivo, alone or combined with autologous or allogenic live cells, for example. The conditioned medium, if introduced in vivo, may be introduced locally at a site of treatment, or remotely to provide needed cellular growth or trophic factors to a patient. This same medium may also be used for the maturation of the TEBVs. Alternatively, hUTC or other cells conditioned medium may also be lyophilized onto the scaffolds prior to seeding with both ECs and SMCs.

From a manufacturing perspective, hUTCs or other cells, or conditioned medium may shorten the time for the in vitro culture or fabrication of TEBVs. This will also result in the use of less starting cells making autologous sources of ECs and SMCs a more viable option.

In one embodiment, the tissue engineered blood vessels comprising a scaffold and one or more of cells, cell sheets, cell lysate, or minced tissue is enhanced by combining with bioactive agents. These tissue engineered blood vessels may be cultured with or without a bioreactor process. The TEBV scaffolds may be cultured using various cell culture bioreactors, including but not limited to a spinner flask, a rotating wall vessel (RWV) bioreactor, a perfusion-based bioreactor or combination thereof. In one embodiment the cell culture bioreactor is a rotating wall vessel (RWV) bioreactor or a perfusion-based bioreactor. The perfusion-based bioreactor will consist of a device for securing the TEBV scaffolds and allow culture medium to flow through the lumen of the scaffolds, and may also allow for seeding and culturing of cells on both the inner (lumen) and outer surfaces of the scaffolds. The perfusion bioreactors may also have the capability of generating pulsatile flow and various pressures for conditioning of the cell-seeded scaffolds prior to implantation. pulsatile flow stress during bioreactor process (1-25 dynes/cm$^2$ over 1 day-1 yr preferable; more preferably a gradual increase from 1-25 dynes/cm$^2$ over 2-4 wks).

The scaffolds having cells, cell sheets, cell lysate, or minced tissue and optionally bioactive agents may be cultured for longer a period, e.g. greater than one day, to allow for cell proliferation and matrix synthesis within the scaffold prior to implantation. Cells cell sheets, cell lysate, or minced tissue are applied to the scaffold as described herein above and transferred to the bioreactor for longer term culture, or more preferably, seeded and cultured within the bioreactor. Multiple bioreactors may be also used sequentially, e.g. one for initial seeding of cells, and another for long-term culture.

The process of seeding and culturing cells with a scaffold using a bioreactor may be repeated with multiple cell types sequentially, e.g. smooth muscle cells are seeded and cultured for a period of time, followed by seeding and culture of endothelial cells, or simultaneously (e.g. smooth muscle cells on the outer surface, and endothelial cells with on the inner surface (lumen) of the scaffolds). The construct may or may not be cultured for a period of time to promote maturation. The bioreactor conditions can be controlled as to promote proper maturation of the construct. Following the culture period the construct can be removed and implanted into a vascular site in an animal or human.

General cell culture conditions include temperatures of 37° C. and 5% $CO_2$. The cell seeded constructs will be cultured in a physiological buffered salt solution maintained at or near physiological pH. Culture media can be supplemented with oxygen to support metabolic respiration. The culture media may be standard formulations or modified to optimally support cell growth and maturation in the construct. The culture media may contain a buffer, salts, amino acids, glucose, vitamins and other cellular nutrients. The media may also contain growth factors selected to establish endothelial and smooth muscle cells within the construct. Examples of these may include VEGF, FGF2, angiostatin, endostatin, thrombin and angiotensin II. The culture media may also be perfused within the construct to promote maturation of the construct. This may include flow within the lumen of the vessel at pressures and flow rates that may be at or near values that the construct may be exposed to upon implant.

The media is specific for the cell type being cultured (i.e., endothelial medium for endothelial cells, and smooth muscle cell medium for SMCs). For the perfusion bioreactor especially, there are other considerations taken into account such as but not limited to shear stress (related to flow rate), oxygen tension, and pressure.

The TEBVs can be also be electrically stimulated to enhance the attachment or proliferation of the different cell types. The electrical stimulation can be performed during the culture and expansion of the cells prior to the fabrication of the TEBV, during the maturation phase of the TEBV, or during implantation. Cells, including hUTCs may also be electrically stimulated during the production of conditioned medium.

The present invention also provides a method for the repair or regeneration of tissue inserting the TEBV described above at a location on the blood vessel in need of repair. These TEBV structures are particularly useful for the regeneration of tissue between two or more different types of tissues. For a multi-cellular system in the simplest case, one cell type could be present on one side of the scaffold and a second cell type on the other side of the scaffold. Examples of such regeneration can be (a) vascular tissue with smooth muscle on the outside and endothelial cells on the inside to regenerate vascular structures.

The invention also relates to methods of treating tissue using the TEBV prepared by the methods described herein. The TEBV can be used in arteriovenous grafting, coronary artery grafting or peripheral artery grafting. For example, in a typical AV (arteriovenous) surgical procedure used for the treatment of end-stage renal failure patients, the surgeon makes an incision through the skin and muscle of the forearm. An artery and a vein are selected (usually the radial artery and the cephalic vein) and an incision is made into each. The TEBV is then used to anastomos the ends of the artery and the vein. The muscle and skin are then closed. After the graft has properly healed (4-6 weeks), the successful by-pass can be used to treat the patients blood.

In a coronary by-pass (CABG) procedure, a TEBV would be used for patients suffering from arteriosclerosis, a common arterial disorder characterized by arterial walls that have thickened, have lost elasticity, and have calcified. This leads to a decrease in blood supply which can lead to damage to the heart, stroke and heart attacks. In a typical CABG procedure, the surgeon opens the chest via a sternotomy. The heart's functions are taken over by a Heart and Lung machine. The diseased artery is located and one end of the TEBV is sewn onto the coronary arteries beyond the blockages and the other end is attached to the aorta. The heart is restarted, the sternum is wired together and the incisions are sutured closed. Within a few weeks, the successful by-pass procedure is fully healed and the patient is functioning normally.

The following examples are illustrative of the principles and practice of this invention, although not limited thereto. Numerous additional embodiments within the scope and spirit of the invention will become apparent to those skilled in the art once having the benefit of this disclosure.

EXAMPLES

Example 1

Tubular Scaffolds of Bioabsorbable Polymers Fabricated by Electrospinning Processes PDO Electrospun Tubes
1) From High Concentration (140 mg/ml)

Solutions of 140 mg/mL of poly(p-dioxanone) (PDO) (Ethicon, Inc., Somerville, N.J.) were made with 1,1,1,3,3,3-hexafluoro-2-propanol (HFP, TCI America Inc., Portland, Oreg.) solvent. Solutions were left in a box (dark environment) overnight on a shaker plate to ensure that all PDO had dissolved and formed a homogenous solution. 4 mL of polymer solution were then drawn into a plastic syringe (5 ml) (Beckton Dickinson, Franklin Lakes, N.J.) and placed in a syringe pump (KD Scientific Model 100, Holliston, Mass.) to be dispensed at a rate of 8 ml/h. A high voltage power supply (Spellman CZE1000R; Spellman High Voltage Electronics Corporation, Hauppauge, N.Y.)) was used to apply a voltage of +25 kV to a blunt tip 18 gauge needle fixed to the solution containing syringe. Solutions were electrospun onto a 5 mm diameter cylindrical grounded mandrel placed 8 inches from the needle tip and rotating at a rate of ~400 rpm to produce a scaffold of randomly oriented fibers. Mandrel translation distance was 18 cm, with a translational speed of 18 cm/s to ensure even coverage along the length of the mandrel. Immediately after electrospinning, the mandrel and scaffold were quickly immersed in an ethanol bath, and the scaffold was carefully slid off the mandrel. The tube (inner diameter: 5 mm, thickness: ~500 microns, length: 10 cm) was then placed in a fume hood for 30 minutes to allow for the evaporation of any residual ethanol.

2) From Medium Concentration (100 mg/ml)

Solutions of 100 mg/ml of PDO were made by placing the polymer in HFP solvent and leaving the solution overnight in the dark on a shaker plate to ensure that all PDO was dissolved and forms a homogenous solution. The desired volume of polymer solution is then drawn into a plastic Beckton Dickinson syringe and placed in the syringe pump to be dispensed at a rate of 10 ml/hr. Two high voltage power supplies were used. One was used to apply a voltage of +20 kV to a blunt tip 18 gauge needle fixed to the solution containing syringe, while the other provides −8 kV to a flat metal target 5" in diameter placed 6" behind the grounded mandrel (2 or 5 mm in diameter). The grounded mandrel was placed 8" from the needle tip and rotating at a rate of ~400 rpm to produce a scaffold of randomly oriented fibers. Mandrel translation distance was 18 cm, with a translational speed of 18 cm/s. For tubular constructs, immediately after electrospinning the mandrel and scaffold were quickly immersed in an ethanol bath to assist in sliding the tube off the mandrel. Tubes were then placed in a fume hood for 30 minutes to allow for the evaporation of any residual ethanol.

3) From Low Concentration (60 mg/ml)

Solutions of 60 mg/mL of PDO were made with HFP solvent. Solutions were left in a box (dark environment) overnight on a shaker plate to ensure that all PDO had dissolved and formed a homogenous solution. 15 mL of polymer solution were then drawn into a plastic Beckton Dickinson syringe (30 ml) and placed in the syringe pump to be dispensed at a rate of 12 ml/h. Two high voltage power supplies were used. One was used to apply a voltage of +22 kV to a blunt tip 18 gauge needle fixed to the solution containing syringe, while the other provided −10 kV to a flat metal target placed 6 inches behind the grounded mandrel. Solutions were electrospun onto a 5 mm diameter cylindrical grounded mandrel placed 12 inches from the needle tip and rotating at a rate of ~400 rpm to produce a scaffold of randomly oriented fibers. Mandrel translation distance was 18 cm, with a translational speed of 18 cm/s. Immediately after electrospinning, the mandrel and scaffold were quickly immersed in an ethanol bath, and the scaffold was carefully slid off the mandrel. The tube (inner diameter: 5 mm, thickness: ~500 microns, length: 10 cm) was then placed in a fume hood for 30 minutes to allow for the evaporation of any residual ethanol.

85/15 PLGA Electrospun Tubes

1) From High Concentration (120 mg/ml)

Solutions of 120 mg/mL of poly(lactide-co-glycolide) (Purac, Linolnshire, Ill.) having a mole percent ratio of lactide to glycolide of 85/15 (85/15 PLGA) were made with HFP solvent. Solutions were left in a box (dark environment) overnight on a shaker plate to ensure that all 85/15 PLGA had dissolved and formed a homogenous solution. 5 mL of polymer solution were then drawn into a plastic Beckton Dickinson syringe (5 ml) and placed in the syringe pump to be dispensed at a rate of 8 ml/h. Two high voltage power supplies were used. One was used to apply a voltage of +22 kV to a blunt tip 18 gauge needle fixed to the solution containing syringe, while the other provided −10 kV to a flat metal target placed 6 inches behind the grounded mandrel. Solutions were electrospun onto a 5 mm diameter cylindrical grounded mandrel placed 8 inches from the needle tip and rotating at a rate of ~400 rpm to produce a scaffold of randomly oriented fibers. Mandrel translation distance was 18 cm, with a translational speed of 18 cm/s. Prior to electrospinning, the mandrel was wrapped with a small section of aluminum foil to aid in tube removal. Upon completion of electrospinning, the foil liner was slid off the mandrel, and carefully removed from the inside of the tube (inner diameter: 5 mm, thickness: ~500 microns, length: 10 cm).

2) From Low Concentration (50 mg/ml)

Solutions of 50 mg/mL of 85/15 PLGA were made with HFP solvent. Solutions were left in a box (dark environment) overnight on a shaker plate to ensure that all 85/15 PLGA had dissolved and formed a homogenous solution. 15 mL of polymer solution were then drawn into a plastic Beckton Dickinson syringe (30 ml) and placed in the syringe pump to be dispensed at a rate of 12 ml/h. Two high voltage power supplies were used. One was used to apply a voltage of +22 kV to a blunt tip 18 gauge needle fixed to the solution containing syringe, while the other provided −5 kV to a flat metal target placed 6 inches behind the grounded mandrel. Solutions were electrospun onto a 5 mm diameter cylindrical grounded mandrel placed 8 inches from the needle tip and rotating at a rate of ~400 rpm to produce a scaffold of randomly oriented fibers. Mandrel translation speed was set to 18 cm/s. Prior to electrospinning, the mandrel was wrapped with a small section of aluminum foil to aid in tube removal. Upon completion of electrospinning, the foil liner was slid off the mandrel, and carefully removed from the inside of the tube (inner diameter: 5 mm, thickness: ~500 microns, length: 10 cm).

Example 2

Tubular Scaffolds of Bioabsorbable Polymers and Collagen Fabricated by Electrospinning Processes 1) Collagen Electrospun Tubes Collagen (Bovine Collagen Type I, Kensey Nash, Exton, Pa.) was electrospun at a concentration of 120 mg/ml in HFP. Collagen solutions were mixed and allowed to sit overnight inside a dark box placed on a shaker plate to ensure that all collagen was dissolved. For collagen tubes, a small volume (0.2-0.5 ml depending on mandrel diameter) of collagen solution was drawn into a 1 ml Beckton Dickinson syringe and electrospun onto the rotating mandrel to aid in tube removal. This preliminary coating of collagen was dispensed through a blunted 18 gauge needle at a rate of 3 ml/hr. The two high voltage power supplies were connected to the needle tip and the 5" diameter back target placed 6" behind the mandrel (2 or 5 mm in diameter), and are set to +25 kv and −10 kv, respectively. The grounded mandrel was placed 8" from the charged needle tip, and rotates at a rate of ~400 rpm to produce a scaffold of randomly oriented fibers. Mandrel translation distance was 18 cm, with a translational speed of 18 cm/s. Upon completion of the preliminary sacrificial layer of collagen, the initial syringe was disposed of and a new syringe containing the desired volume of collagen solution was placed on the syringe pump. This solution was electrospun using the same parameters as the sacrificial layer. Upon completion of the electrospinning process, the mandrel was removed from the electrospinning chamber, and the graft was carefully slid off the mandrel. During this process the initial layer was torn away from the graft, leaving a thin layer of collagen still on the mandrel.

2) PDO and Collagen Electrospun Tubes

50:50 PDO:collagen scaffolds are scaffolds composed of a 50:50 ratio by volume of 100 mg/ml PDO and 120 mg/ml collagen (Bovine Collagen Type I, Kensey Nash, Exton, Pa.) solutions. The two polymer solutions were made in separate scintillation vials under conditions identical to those of electrospinning the polymers individually by placing the polymers in HFP solution overnight in a dark box on a shaker plate. Once the polymers had completely dissolved equal volumes of the two solutions were combined together in a new scintillation vial, vortexed for 30 seconds, and placed on a shaker. While the two solutions were mixing, a small volume of pure collagen solution is electrospun onto the grounded mandrel to serve as a sacrificial layer using a process identical to that in the above protocol for electrospinning pure collagen tubes. Once the preliminary collagen layer had been electrospun, the desired volume of blended PDO:collagen solution was drawn into a Beckton Dickinson syringe and electrospun onto the rotating mandrel (2 or 5 mm in diameter) to aid in tube removal. Upon completion of the preliminary sacrificial layer of collagen, the initial syringe was disposed of and a new syringe containing the desired volume of collagen solution was placed on the syringe pump. This solution was electrospun using the same parameters as the sacrificial layer and as described in example 2, part 1.

3) Cross-Linking Collagen and PDO:Collagen ESS Tubes with 1-ethyl-3-(3-dimethylaminopropl)carbodiimide hydrochloride (EDC)

Pure collagen scaffolds, as well as blends of PDO and collagen prepared in example 2, parts 2 and 3 were cross-linked using 1-ethyl-3-(3-dimethylaminopropyl)carbodiimide hydrochloride (EDC) in pure ethanol. Samples were soaked in a 40 mM (50× the molar concentration of collagen in HFP) solution of EDC in ethanol for 18 hrs, followed by a 2 hr rinse in 0.1 M disodium phosphate solution to hydrolyze any unreacted O-isoacylurea intermediates. After cross-linking, samples were rinsed in de-ionized water, frozen, and lyophilized overnight to remove any residual moisture.

Example 3

PDO Sheet Scaffolds of Bioabsorbable Polymers Fabricated by Electrospinning Processes Solutions of 100 mg/ml of PDO were made by placing the polymer in HFP solvent and leaving the solution overnight in dark box on a shaker plate to ensure that all PDO was dissolved and forms a homogenous solution. The desired volume of polymer solution was then drawn into a plastic Beckton Dickinson syringe and placed in the syringe pump to be dispensed at a rate of 10 ml/hr. Two high voltage power supplies were used. One was used to apply a voltage of +20 kV to a blunt tip 18 gauge needle fixed to the solution containing syringe, while the other provides −8 kV to a metal target placed 6" behind the grounded mandrel (2.5 cm in diameter). The grounded mandrel was placed 8" from the needle tip and rotating at a rate of ~400 rpm to produce a scaffold of randomly oriented fibers. Mandrel translation distance was 18 cm, with a translational speed of 18 cm/s. Immediately after electrospinning the mandrel and scaffold are quickly immersed in an ethanol bath to assist in sliding the tube off the mandrel. The tube is cut to form a sheet and then placed in a fume hood for 30 minutes to allow for the evaporation of any residual ethanol.

Example 4

50:50 PDO:Collagen Sheet Scaffolds of Bioabsorbable Polymers and Collagen Fabricated by Electrospinning Processes 50:50 PDO:collagen scaffolds are scaffolds composed of a 50:50 ratio by volume of 100 mg/ml PDO and 120 mg/ml collagen solutions and were made by a process as described in Example 3.

The 50:50 PDS:Collagen sheets were then cross-linked using 1-ethyl-3-(3-dimethylaminopropyl)carbodiimide hydrochloride (EDC) in pure ethanol. Samples were soaked in a 40 mM (50× the molar concentration of collagen in HFP) solution of EDC in ethanol for 18 hrs, followed by a 2 hr rinse in 0.1 M disodium phosphate solution to hydrolyze any unreacted O-isoacylurea intermediates. After cross-linking, samples were rinsed in de-ionized water, frozen, and lyophilized overnight to remove any residual moisture.

Example 5

Tubular Scaffolds of Bioabsorbable Polymers Fabricated by a Lyophilization Processes 1) 35/65 poly(caprolactone-co-glycolide) (35/65 PCL/PGA) Lyophilized Tubes (10 wt % Solution in 1,4-dioxane)

This example describes the making of a tube containing porous structures that would provide pathways for nutrient transport and guided tissue regeneration. Hence, a 10% wt./wt. polymer solution was prepared by dissolving 1 part 35/65 PCL/PGA (Ethicon, Inc., Somerville, N.J.) with 9 parts of solvent 1,4-dioxane. The solution was prepared in a flask with a magnetic stir bar. To dissolve the copolymer completely, the mixture was gently heated to 60° C. and continuously stirred overnight. A clear homogeneous solution was then obtained by filtering the solution through an extra coarse filter (Pyrex brand extraction thimble with fritted disc).

A lyophilizer (DURA-STOP, FTS Systems, Stone Ridge, N.Y.) was used to then form the tubes from the polymer solution. The freeze dryer was powered up and the shelf chamber was maintained at −17° C. for approximately 30 minutes. Thermocouples to monitor the shelf temperature were attached for monitoring. The homogeneous polymer solution prepared in Step A was poured into a gap between the barrel of a 1 ml Beckton Dickinson (BD) syringe and the plunger of 1 ml BD syringe, thereby using the syringe as a mold to form the tube. The mold was placed into the lyophilizer maintained at −17° C. (pre-cooling). The lyophilization cycle was started and the shelf temperature was held at −17° C. for 15 minutes and then, held at −15° C. for 120 minutes. A vacuum was applied to initiate drying of the dioxane by sublimation. The shelf temperature was raised to −5° C. and held at this temperature for 60 minutes. The shelf temperature was raised to 5° C. and held for 60 minutes. The shelf temperature was raised again to 20° C. and held at that temperature for 60 minutes. A second stage of drying was started and the shelf temperature was held at 20° C. for an additional 120 minutes. At the end of the second stage, the lyophilizer was brought to room temperature and atmospheric pressure. The thin scaffold was removed from the plunger of the syringe.

2) 35/65 poly(caprolactone-co-glycolide) (35/65 PCL/PGA) Lyophilized Tubes (5 wt % Solution in 1,4-dioxane)

This example describes the making of a tube containing porous structures that would provide pathways for nutrient transport and guided tissue regeneration. Hence, a 5% wt./wt. polymer solution was prepared by dissolving 1 part 35/65 PCL/PGA with 9 parts of solvent 1,4-dioxane. The solution was prepared in a flask with a magnetic stir bar. To dissolve the copolymer completely, the mixture was gently heated to 60° C. and continuously stirred overnight. A clear homogeneous solution was then obtained by filtering the solution through an extra coarse filter (Pyrex brand extraction thimble with fritted disc).

A lyophilizer (DURA-STOP, FTS systems, Stone Ridge, N.Y.) was used to then form the tubes from the polymer solution. The freeze dryer was powered up and the shelf chamber was maintained at −17° C. for approximately 30 minutes. Thermocouples to monitor the shelf temperature were attached for monitoring. The homogeneous polymer solution prepared in Step A was poured into a gap between the barrel of a 1 ml BD syringe and the plunger of 1 ml BD syringe, thereby using the syringe as a mold to form the tube. The mold was placed into a lyophilizer maintained at −17° C. (pre-cooling). The lyophilization cycle was started and the shelf temperature was held at −17° C. for 15 minutes and then, held at −15° C. for 120 minutes. A vacuum was applied to initiate drying of the dioxane by sublimation. The shelf temperature was raised to −5° C. and held at this temperature for 60 minutes. The shelf temperature was raised to 5° C. and held for 60 minutes. The shelf temperature was raised again to 20° C. and held at that temperature for 60 minutes. A second stage of drying was started and the shelf temperature was held at 20° C. for an additional 120 minutes. At the end of the second stage, the lyophilizer was brought to room temperature and atmospheric pressure. The thin scaffold was removed from the plunger of the syringe.

Example 6

Preparation of Poly(Lactide) and Poly(Glycolide) Non-Woven Tubes

Nonwoven tubes possessing a length of approximately 50 mm and an internal diameter of approximately 4 mm and a wall thickness of approximately 0.5-1.0 mm were fabricated from various bioresorbable filaments. Specifically, filaments were comprised of poly(lactide) (PLA) and poly(glycolide) (PGA) and a copolymer of PGA and PLA in a 90:10 molar ratio (90/10 PGA/PLA). These samples were fabricated using a dry lay nonwoven technique to first produce a non-woven batt from filaments approximately 20 microns in diameter

Example 7

Preparation of a Collagen Coated Absorbable, Synthetic Tissue Engineered Tubular Scaffold Highly purified atelocollagen (Colbar, a Johnson & Johnson Co., Israel) is used for coating a tissue engineered tubular scaffold, prepared as described in Examples 1-6 and 8-11. The tissue engineered tubular scaffold (Example 1, part 2) was placed on a mandrel and immersed in 10 mM HCl solution containing 1 mg/ml collagen. The tissue engineered tubular scaffold was soaked in the collagen solution for 30 minutes at room temperature. The tissue engineered tubular scaffold was removed from the solution and dried at room temperature for 8 hours.

Example 8

Preparation of an Acellular Omental Matrix Coated Tissue Engineered Tubular Scaffold Pig omentum is placed in 0.9% saline after harvest. After rinsing in the saline solution 3 times to rinse off blood and other extraneous debris, the omentum is placed in 70% ethanol for 30 minutes. Following the treatment with 70% ethanol, the tissue is dehydrated in 100% ethanol for 30 minutes with two changes into fresh ethanol. The tissue is then transferred to acetone for 180 minutes, using fresh solution every 60 minutes. Subsequently, the tissue is placed in a 50:50 acetone-hexane mixture for 60 minutes, followed by a 20:80 mixture of the same for 24-48 hours (with 3 changes of fresh solution) for lipid removal. The tissue is then transferred to 100% ethanol for 30 minutes and subsequently to 70% ethanol where, if necessary, it could be stored at 4° C. until the decellularization process is initiated. The tissue is then immersed in a decellularization buffer comprising TRITON® X-100 (1% w/V; a nonionic detergent) (Sigma-Aldrich, St. Louis, N.J.) and $MgCl_2$ (1%) dissolved in 50 mM Tris-HCl (pH 7.2), for 30 minutes. This is followed by treatment in an enzyme solution comprising endonuclease (BENZONASE; 41.8 U/ml, Sigma-Aldrich, St. Louis, N.J.) mixed with the decellularization buffer. The tissue is spun in this solution for 20 hours. The tissue is then washed twice (2 hours each) in a solution comprising 50 mM Tris-HCl (pH 7.2), 5 mM $MgCl_2$ and 1% (W/V) TRITON® X-100. The tissue is then placed in a cell extracting solution comprising 1M NaCl, 20 mm EDTA, 0.2% (W/V) TRITON® X-100 pH 7.0 for 1 hr, following which the tissue is washed with ultra pure water (4 times, 5 minutes each). The tissue is transferred to disinfection solution comprising 80:20 water:ethanol (200 proof) with 0.15% peracetic acid (or acetic acid) for 1 hour after washing in water (4 times, 20 minutes each), the tissue is stored in 70% alcohol at 4° C.

The acellular omentum is air dried and then cryogenically milled into a powder. The powder is then dispersed into 10 mM HCl at a concentration of 5 mg/ml. A tissue engineered tubular scaffold, as described in Examples 1-6 and 9-11 is placed onto a mandrel and immersed in the acellular omentum suspension and dried by lyophilization at −20° C. for 24 hours. The omental matrix on the impregnated tissue engineered tubular scaffold is then cross linked by thermal dehydration at 120° C. overnight under vacuum.

and approximately 50 mm in length. This batt was then consolidated via needle punching using a mandrel.

Example 9

Generation of Cell Sheets on PCL/PGA Films

This example describes the generation of cells sheets comprised of Human umbilical vein endothelial cells (HUVECs) on films. These sheets can then be fabricated into tubular structures leading to TEBV comprised solely of human umbilical vein endothelial cells (HUVEC). Human umbilical vein endothelial cells (HUVEC) were seeded onto PCL/PGA films to obtain cell sheets. To do this, films were cast by adding 2.5 ml of the polymer solution (45/55 PCL/PGA 10% (w/w) in dioxane or 35/65 PCL/PGA 10% (w/w) in dioxane) onto a 60 mm culture dishes. After casting, films were sterilized by washing in ethanol and air-dried. HUVEC were harvested by trypsinization and counted using a Guava instrument (Guava Technologies, Hayward, Calif.). Cells were seeded onto the films at a density of 5000 cells/$cm^2$ (141,350 cells/60 mm dish) and then placed in a 37° C. incubator for 9 days. Cells were visualized by microscopy or by calcein staining. The HUVEC cells grew to a confluent layer on a poly(caprolactone-co-glycolide 35/65 mole-mole %) (35/65 PCL/PGA) film or a poly(caprolactone-co-glycolide 45/55 mole-mole %) (45/55 PCL/PGA) film providing a cell sheet. Microscopic images confirmed there was a confluent monolayer of cells. Calcein staining showed cells attached and proliferated at days 9 with little to no evidence of dead cells.

The sheets can be rolled into a tube to form a construct that can be used as a tissue engineered blood vessel alone or in combination with a mechanical strut such as the scaffolds described in Examples 1-8 or 11. By similar methods (see examples 18 and 19), cell sheets can be formed into a tube directly.

Example 10

Generation of Cell Sheets on PCL/PGA Films

This example describes the generation of cells sheets comprised of human umbilical tissue derived cells (hUTCs) on films. Human umbilical tissue-derived cells are obtained by methods described in U.S. Pat. No. 7,510,873 incorporated by reference in its entirety. These sheets are fabricated into tubular structures leading to TEBV comprised solely of hUTC. hUTCs are seeded onto PCL/PGA films to obtain cell sheets. To do this, films are cast by adding 2.5 ml of the polymer solution onto a 60 mm culture dishes. After casting, films are sterilized by washing in ethanol and air-dried. hUTCs are harvested by trypsinization and counted using a Guava instrument. Cells are seeded onto the films at a density of 5000 cells/$cm^2$ (141,350 cells/60 mm dish) and are then placed in a 37° C. incubator. Cells are visualized by microscopy or by calcein staining. Cell sheets comprised of hUTCs and a poly(caprolactone-co-glycolide 35/65 mole-mole %) (35/65 PCL/PGA) film or a poly(caprolactone-co-glycolide 45/55 mole-mole %) (45/55 PCL/PGA) film are prepared.

The sheets can be rolled into a tube to form a construct that can be used as a tissue engineered blood vessel alone or in combination with a mechanical strut such as the scaffolds described in Examples 1-8 or 11. By similar methods (See examples 18 and 19), cell sheets can be formed into a tube directly.

Example 11

Lyophilized, Decellularized Cell Sheets

This example relates to the use of lyophilized or decellularized cell sheets to fabricate TEBV. The cell sheets will be generated in vitro and then lyophilized or decellularized. When needed, the required type of cell sheets can be thawed and then formed into tubular structures to produce TEBV. Decellularized cell sheets, on the other hand, can be wrapped around other cell sheets to enhance the construction of TEBV by providing trophic factor support or extracellular matrix proteins.

Cell sheets will be generated as in Examples 9, 10 and 17. Alternative methods of obtaining cell sheets will include culturing cells on decellularized omentum (Example 8), on tissue-culture plastic, or on thermoresponsive dishes (CellSeed, Inc, Tokyo, Japan). Cell types used for obtaining cell sheets will include endothelial cells, smooth muscle cells, skeletal muscle cells, or hUTC. Cells will be maintained in culture until a monolayer is achieved. The resulting cell sheets will then be processed for vitrification by cryopreservation and subsequent lyophilization (Core Dynamics, Orangeburg, N.Y.).

Example 12

Attachment and Growth of Human Umbilical Tissue-Derived Cells on PDO ESS Scaffolds This example relates to the use of human umbilical tissue-derived cells (hUTC) to produce tissue-engineered blood vessels (TEBVs). TEBVs can be generated by seeding vascular grafts or scaffold materials with human umbilical tissue-derived cells. It is envisioned that seeding hUTC onto the TEBVs will enhance the seeding, attachment, and proliferation of endothelian cells (ECs) and smooth muscle cells (SMCs) when seeded in vitro or onto the vascular grafts after implantation. hUTC may also promote the infiltration and subsequent differentiation of the EC or SMC progenitor cells into the graft construct. This may promote the maturation and the engraftment of TEBVs during the in vivo implantation by providing trophic support, or providing the expression of ECM proteins.

Attachment and growth of hUTC on PDO and PDO/collagen (50/50, crosslinked) (Examples 1 and 2) ESS scaffolds were assessed. Biopsy punches 5 mm in diameter were made from the scaffold materials and pre-wet in complete growth medium. hUTC were then trypsinized, counted and resuspended at a concentration of 200,000 cells/ml in complete growth medium. The scaffold punches were placed in 96-well low cluster plates and seeded with 100 microliters of the cell suspension (20,000 cells/punch). Cells were allowed to attach for 3 hours at 37° C., and then the scaffolds were transferred to 24-well low cluster plates containing 1 ml of complete growth medium. The scaffolds were cultured for 7 days with a medium change after 3 days.

On day 3 and day 7 post-seeding, the scaffolds were transferred to fresh low cluster 24-well dishes containing 1 ml serum-free DMEM. The scaffolds were then washed with an additional 1 ml serum-free DMEM. A stock solution of Live/Dead stain (Invitrogen, Carlsbad, Calif.) containing 2 micromolar calcein AM and 4 micromolar ethidum homodimer was prepared and 0.5 ml was added to each well. After incubation at room temperature for 5 minutes, cell attachment and viability of cells was assessed by fluorescence microscopy.

Results:

The hUTC attached and grew on the TEBV scaffolds. PDO/collagen-ESS scaffolds exhibited more significant increase in the number of cells from day 3 to day 7 as compared to the PDO-ESS scaffolds (FIG. 1).

Example 13

Attachment and Growth of Human Umbilical Artery Smooth Muscle Cells (UASMCs) and Human Umbilical Vein Endothelial Cells (HUVECs) on PDO ESS Scaffolds Attachment and growth of human umbilical artery smooth muscle cells (UASMCs) and human umbilical vein endothelial cells (HUVECs) on PDO ESS scaffolds (100 mg/ml and 140 mg/ml, Example 1) was assessed. UASMCs (Lonza Rockland Inc., Rockland, Me.) and HUVECs (Lonza Rockland Inc., Rockland, Me.) were seeded onto PDO ESS scaffolds, and at specified time points (day 3 and day 7) cells grown on the different surfaces were assessed for viability by Live/Dead staining.

Sterile PDO scaffolds (5 mm biopsy punches) were placed into empty low cluster 96-well dishes, washed with PBS, and then soaked in appropriate medium (EGM-2 for HUVECs, and SmGM for UASMCs) while trypsinizing cells. UASMCs and HUVECs were harvested by trypsinization, counted and resuspended to a final density of $5 \times 10^5$ cells/ml in SmGM (UASMC) or EGM-2 (HUVEC) medium. One hundred microliters (50,000 cells) of this stock cell suspension was aliquotted onto the scaffolds, and the cells were allowed to attach for 3 hours in 37° C. incubator. The scaffolds were then transferred to 24-well dishes containing 1 ml of the appropriate medium and cultured for 3 and 7 days.

The scaffolds were transferred to fresh low cluster 24-well dishes containing 1 ml serum-free DMEM. The graft materials were then washed with an additional 1 ml serum-free DMEM. A stock solution of Live/Dead stain containing 2 micromolar calcein AM and 4 micromolar ethidum homodimer in was prepared serum-free DMEM and 0.5 ml was added to each well. After incubation at room temperature for 5 minutes, cell attachment and viability of cells was assessed by fluorescence microscopy.

Figure 2:
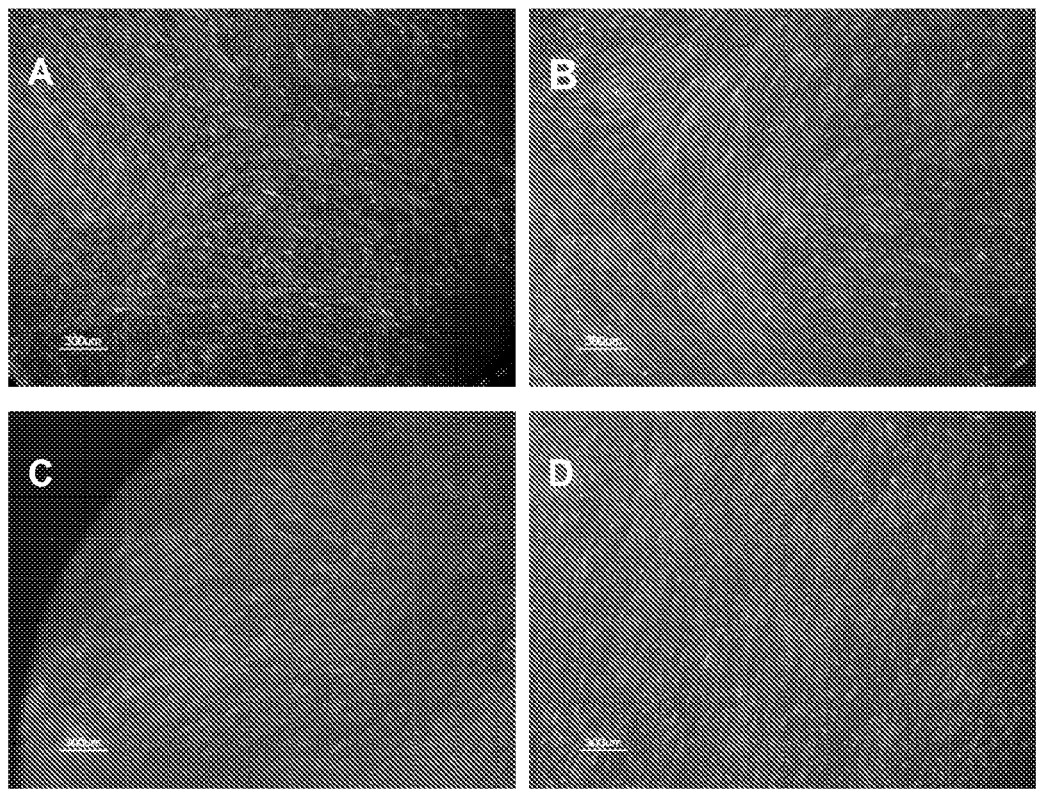
Figure 3:
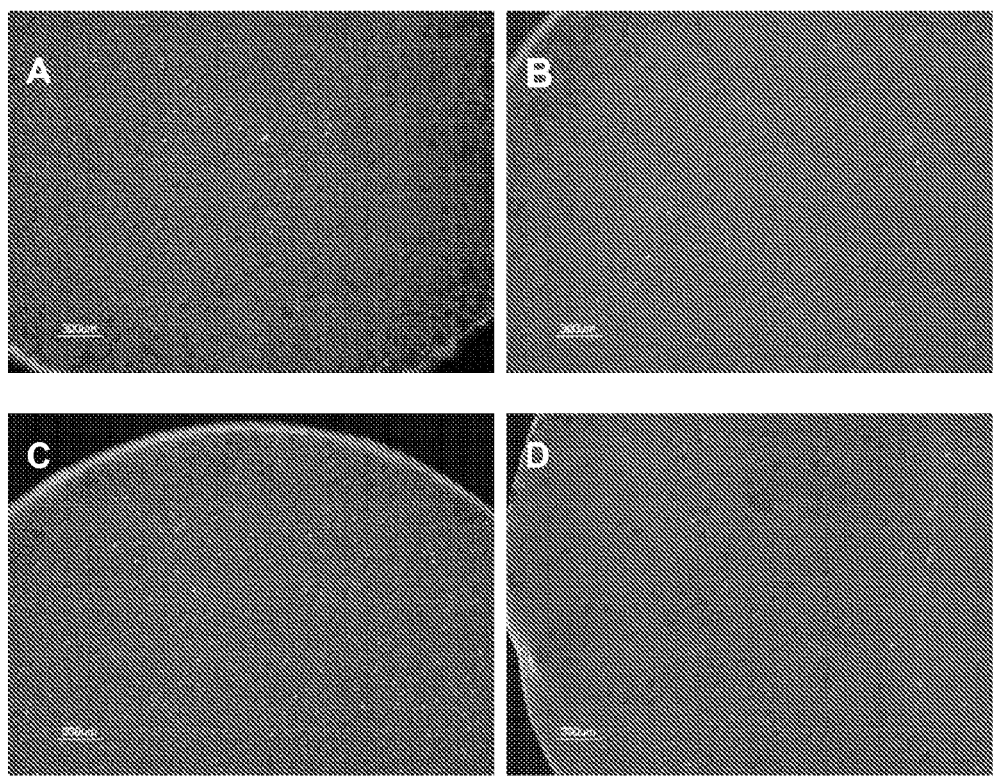
FIG. 3. Representative example of endothelial cell (HUVEC) cell attachment and growth on a vascular graft biomaterial after 3 and 7 days in culture. A: 100 mg/ml PDO-ESS scaffold after 3 days, B: 100 mg/ml PDO-ESS scaffold after 7 days, C: 140 mg/ml PDO-ESS scaffold after 3 days, D: 140 mg/ml PDO-ESS scaffold after 7 days. All images taken at 40× magnification.

Results:

All samples showed cell attachment and growth over the 7 day culture period (FIGS. 2 and 3). The endothelial cells formed an intact monolayer on the surface of the scaffolds. The 100 mg/ml PDO scaffold exhibited the best results, with a high number of attached cells at day 3 and increases in cell number on day 7. The 140 mg/ml PDO scaffold showed a high number of attached cells on day 3, but the increase in cells by day 7 was not as dramatic as the 100 mg/ml scaffold.

Example 14

Effect of hUTCs on Proliferation and Migration of HUVECs

This example relates to the use of human umbilical tissue-derived cells (hUTCs) to produce tissue-engineered vascular grafts (TEBVs). TEBVs can be generated by seeding vascular grafts or scaffold materials with human endothelial cells (ECs) and human smooth muscle cells (SMCs). It is envisioned that hUTCs will enhance the seeding, attachment, and proliferation of ECs and SMCs on the vascular grafts. hUTCS may also promote the differentiation of the EC or SMC or progenitor cells in the graft construct. This may promote the maturation of TEBVs during the in vitro culture as well as the engraftment during the in vivo implantation. hUTCs may provide trophic support, or provide and enhance the expression of ECM proteins.

As proof of principle, the effects of hUTC on the proliferation and migration of HUVEC are investigated in vitro.

For studies of proliferation, the effects of hUTC lot#120304 were tested and three endothelial cell types from different vascular beds were used as responder cells (human umbilical vein endothelial cells [HUVEC], human coronary artery endothelial cells [HCAEC], and human iliac artery endothelial cells [HIAEC]). Co-culture with hUTC resulted in enhanced proliferation of endothelial cells. Co-culture with mesenchymal stem cells (MSC) or fibroblasts resulted in cell numbers comparable to media controls (Table 1).

Migration was quantitated by counting the number of cells that were on the underside of a transwell and both HUVEC and HCAEC were used as responder cells. Unlike the studies with proliferation, the migratory responses of these cells are slightly different. HUTC lot#120304 induced the migration of both HUVEC and HCAEC. MSC did not induce the migration of HUVEC suggesting specificity of this response to hUTC (Table 2).

TABLE 1

Effect of hUTC lot#120304, MSC, and fibroblasts on the proliferation of endothelial cells. Endothelial cells (human umbilical vein endothelial cells, human iliac artery endothelial cells, human coronary artery endothelial cells) were seeded onto the bottom of a 24-well tissue culture dish at a density of 5000 cells/cm$^2$ (10,000 cells/well) and hUTC lot#120304, MSC, or fibroblasts inside transwell inserts at a density of 5000 cells/cm$^2$ (1,650 cells/insert) in co-culture media (Hayflick 80% + EGM-2MV 20% or Hayflick 50% + EGM-2MV 50%). After 7 days of co-culture, cells were harvested and counted using a Guava instrument. Endothelial cells were also maintained in EGM-2MV media as positive control.

| | HUVEC | | HIAEC | | HCAEC | |
|---|---|---|---|---|---|---|
| | average | std dev | average | std dev | average | std dev |
| EGM-2MV 100% | 36511.33 | 1307.32 | 18100 | 1609.9413 | 27328 | 3802 |
| Hay80/EGM20 (H80) | 6532.33 | 625.94 | 8770.6667 | 187.37752 | 7391 | 978 |
| hUTC 120304 (H80) | 13394.67 | 2011.56 | 10961.667 | 1678.5 | 12957 | 445 |
| MSC (H80) | 5674.33 | 716.29 | 9555.6667 | 933.66286 | 8136 | 620 |
| fibroblasts (H80) | ND | ND | 8630 | 1049.4805 | ND | ND |
| Hay50/EGM50 (H50) | 6778.5 | 1175.92 | 21847.5 | 2947.9282 | 7818 | 837 |
| hUTC 120304 (H50) | 26595.667 | 4398.96 | 24577.333 | 3421.4854 | 16056 | 4225 |
| MSC (H50) | 5554.67 | 2801.54 | 16065 | 2181.5799 | 8035 | 2198 |
| fibroblasts (H50) | ND | ND | 12158 | 2113.0894 | ND | ND |

TABLE 2

Effect of hUTCs and MSCs on the migration of endothelial cells. HUVEC or HCAEC were seeded inside transwell inserts at a density of 5000 cells/cm$^2$ (23,000 cells/insert) and hUTC lot#120304 or MSC onto the bottom of a 6-well tissue culture dish at a density of 5000 cells/cm$^2$ (48,000 cells/well) in co-culture media (Hayflick 50% + EGM-2MV 50%). After 7 days of co-culture, cells that were on the underside of the transwell insert were harvested and counted using a Guava instrument. Endothelial cells were also maintained in EGM-2MV media as control.

| | HUVEC | | HCAEC | |
|---|---|---|---|---|
| | average | std dev | average | std dev |
| EGM-2MV | 3125.67 | 1849.46 | 848.33 | 539.13 |
| Hayflick 50% | 805.33 | 323.96 | 1926.67 | 280.42 |
| hUTC 120304 | 2402.33 | 880.1 | 9071.67 | 3792.28 |
| MSC | 383 | 124.65 | ND | ND |

Example 15

Preparation of a Cell Lysate-Augmented Biopsy Punches

In this example, hUTC were culture expanded, harvested, lysed by repeated freeze-thaw cycles, and applied to the bioabsorbable scaffolds of Examples 1-11 and lyophilized. The cell lysate augmented scaffolds can be implanted as such or seeded with cells (as in Examples 16, 17) or minced tissue (Examples 25) and cultured to create tissue engineered blood vessels.

Umbilical Postpartum cells hUTC (Passage 11, lot 120304) were cultured at 5,000 cells per cm squared in T225 cm$^2$ cell culture flasks (CORNING, Cat No 431082, Corning, N.Y.) with complete growth media: DMEM-low glucose (GIBCO, Cat No 11054 Invitrogen, Carlsbad, Calif.), 15% Fetal Bovine Serum (HyClone Cat No SH30070-03 Logan, Utah) and Pen/Strep solution (GIBCO, Cat No 15070). After cells expanded to approximately 25,000 cells per cm$^2$, cells were harvested by TrypLE Select (GIBCO cat No 12563) and collected in 50 ml conical tubes, centrifuged at 300 rcf for 5 minutes and removed the supernatant. The cell pellets were washed 3 times with PBS and then re-suspended in PBS at 1×10' cells/ml for a total volume of 14 ml. This solution was snap frozen in liquid nitrogen, thawed in a 37° C. water bath, centrifuged to remove cell debris, and the resulting supernatant (10 ml) removed and stored. The remaining material was again snap frozen, thawed, and centrifuged as above. The supernatant (2 ml) was removed and stored. The protein concentration of the two supernatants was determined by measuring samples diluted in PBS with the Bradford protein assay kit (BIO-RAD Laboratories Hercules, Calif.). The concentration of the first lysate supernatant (Lot#082908) was 5.2 mg/ml (Lot#082908 low) and the second lysate supernatant was 18 mg/ml (Lot#082908 high).

Biopsy punches 5 mm in diameter were taken from PDO-ESS scaffold sheets (Example 3). These scaffolds were placed into 96 well ultra low cluster plate (COSTAR, cat No 3474 Fisher Scientific, Pittsburgh, Pa.), and 25 microliters cell lysate was loaded onto each disc at protein concentration 5.2 mg/ml (low) or 18 mg/ml (high). The scaffold punches were then lyophilized for 48 hours to remove water.

Cell Attachment: The lysate-augmented scaffolds were placed into 96-well low cluster plates and rehydrated with 25 microliters of EGM-2 medium (Lonza Walkersville, Md.). Human umbilical vein endothelial cells (HUVECs) were tyrpisinized, counted and resuspended to a concentration of 500,000 cells/ml. Each scaffold was seeded with 100 microliters of this cell suspension (50,000 cells) and the cells were allowed to attach for 3 hours at 37° C. After this attachment period, the scaffolds were transferred to 24-well low cluster plates containing 1 ml of EGM-2 medium. The scaffolds were cultured for 3 and 7 days.

At day 3 and day 7 post-seeding scaffolds were analyzed for cell attachment using Live/Dead stain and for cell number using the CyQuant assay (Invitrogen) to measure cellular DNA. For the Live/Dead stain, the scaffolds were transferred to fresh low cluster 24-well dishes containing 1 ml serum-free DMEM. The scaffolds were then washed with an additional 1 ml serum-free DMEM. A stock solution of Live/Dead stain containing 2 micromolar calcein AM and 4 micromolar ethidum homodimer was prepared and 0.5 ml was added to each well. After incubation at room temperature for 5 minutes, cell attachment and viability of cells was assessed by fluorescence microscopy.

For the measurement of cellular DNA, the scaffolds were washed in PBS, then frozen in 150 microliters of PBS in microcentrifuge tubes. The scaffolds were then lyophilized to dryness and resuspended in 150 microliters of papain digestion solution. The samples were then digested overnight at 60° C. The next day, 10 microliters was used to assay for DNA content using the CyQuant NF assay kit (Invitrogen).

Figure 4:
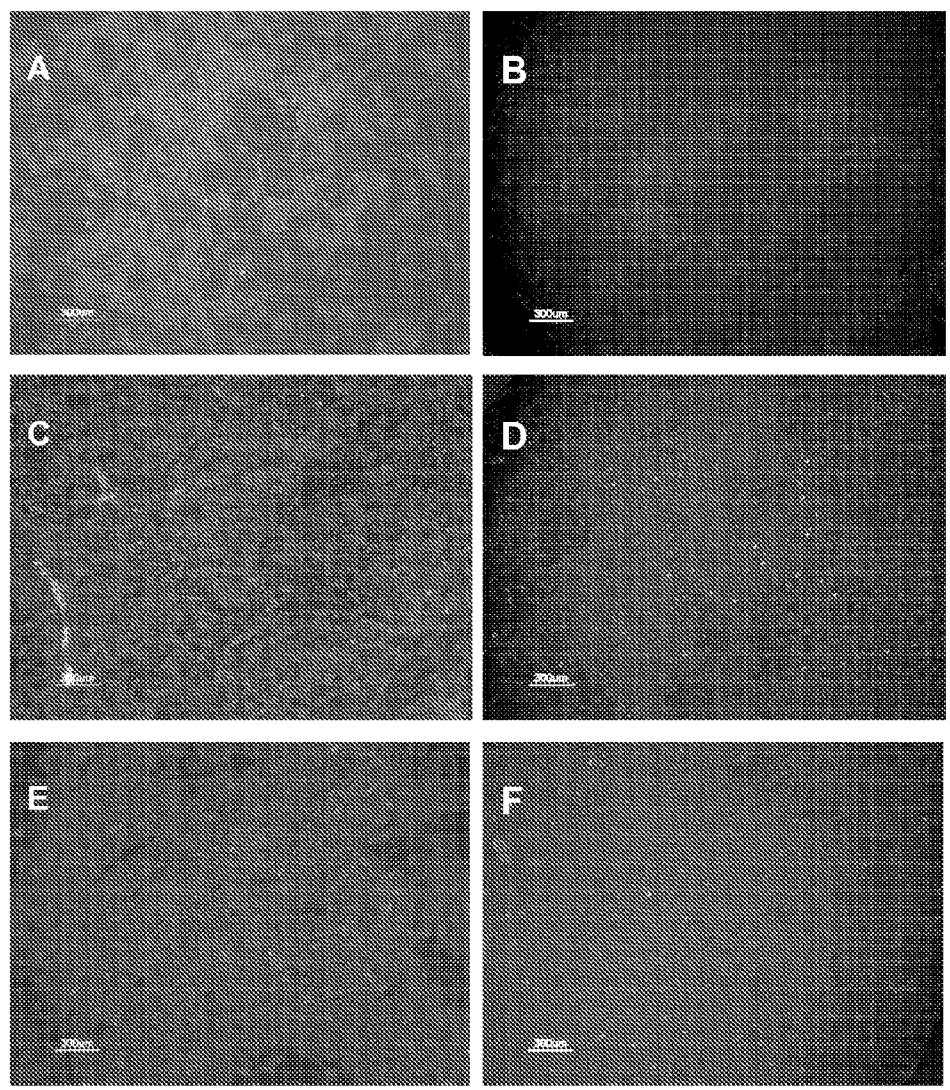
FIG. 4. Cell attachment to lysate-augmented PDO-ESS scaffolds. PDO-ESS scaffolds were loaded with hUTC cell lysate at two different concentrations and lyophilized. Cells (50,000/scaffold) were then seeded onto the scaffolds and cultured for 3 and 7 days before Live/Dead staining. (A) control scaffold after 3 days (B) control scaffold after 7 days (C) 18 mg/ml lysate-augmented scaffold after 3 days (D) 18 mg/ml lysate-augmented scaffold after 7 days (E) 5.2 mg/ml lysate augmented scaffold after 3 days (F) 5.2 mg/ml lysate-augmented scaffold after 7 days. All images taken at 40× magnification.
Figure 5:
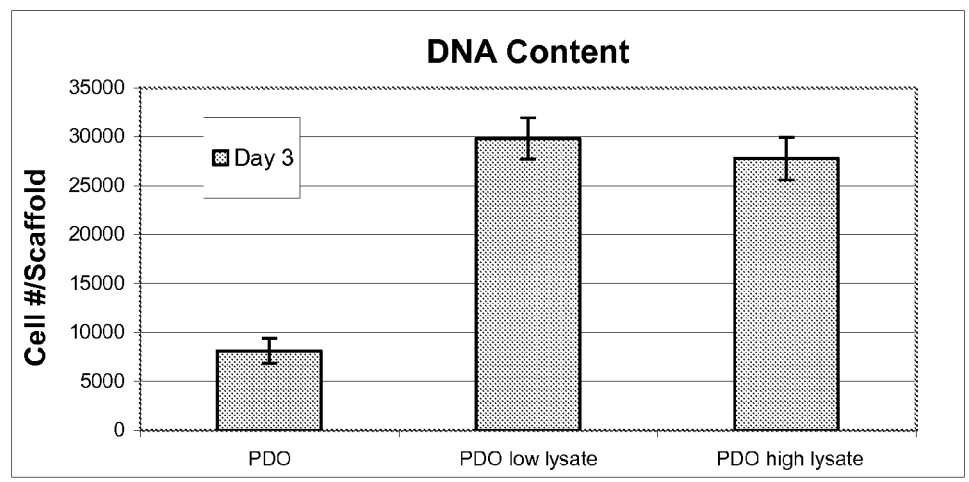
FIG. 5. DNA content of cells cultured on lysate-augmented PDO-ESS scaffolds. PDO-ESS scaffolds were loaded with hUTC cell lysate at two different concentrations (low=5.2 mg/ml, high=18 mg/ml) and lyophilized. Cells (50,000/scaffold) were then seeded onto the scaffolds and cultured for 3 days before analysis of cellular DNA content. Samples were washed, digested with papain and DNA quantitated using the CyQuant NF assay kit.

Results:

An increase in cell number was observed for both concentrations of lysate tested and at both day 3 and day 7 post-seeding. Live/Dead staining shows a greater number of cells and more of the scaffold surface covered at both timepoints examined (FIG. 4). After 3 days there was an approximate 4-fold increase in cellular DNA compared to control scaffolds (FIG. 5).

Example 16

Preparation of Cell Lysate on Tube Scaffolds

PDO tubular scaffolds (Example 1, part 2) were dip-coated into hUTC lysate solution (Example 15) at a protein concentration of 5.2 mg/ml (Lot#082908 Low) for 5 minutes then lyophilized for 24 hours using a lyophilizer DURA-STOP, FTS system. The freeze dryer was powered up and the shelf chamber was maintained at −40° C. for approximately 15 minutes. Thermocouples to monitor the shelf temperature were attached for monitoring. The scaffold tubes were placed into a lyophilizer maintained at −40° C. (pre-cooling). The lyophilization cycle was started and the shelf temperature was held at −40° C. for 15 minutes and then, held at −37° C. for 60 minutes. A vacuum was applied. The shelf temperature was maintained −40° C. and held at this temperature for 180 minutes. The shelf temperature was raised to −25° C. and held for 500 minutes. The shelf temperature was raised to −15° C. and held for 180 minutes. The shelf temperature was raised to −5° C. and held for 180 minutes. The shelf temperature was raised to 5° C. and held for 120 minutes. The shelf temperature was held at 20° C. for 120 minutes. The shelf temperature was held to −20° C. for 120 minutes. After lyophilization, the tubular scaffolds were evaluated for cell attachment.

Figure 6:
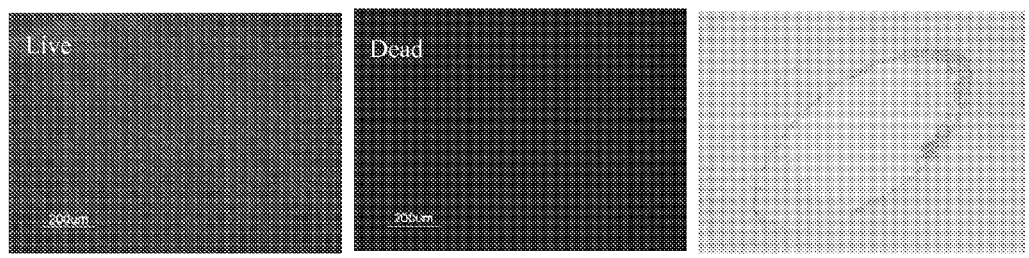
FIG. 6. Tubular scaffolds coated with PBS or hUTC lysate which were cultured with rat SMC for 24 hours showed Lysate coated scaffolds showed more cell attachment from LIVE/DEAD and H&E image FIG. 7. H&E staining for the hUTC seeded PDO sheet pre-coated with hUTC lysate after cultured 11 days after seeding. While cells were only seeded on one side, cells migrated and penetrated all over the scaffold. Box?
Figure 6:
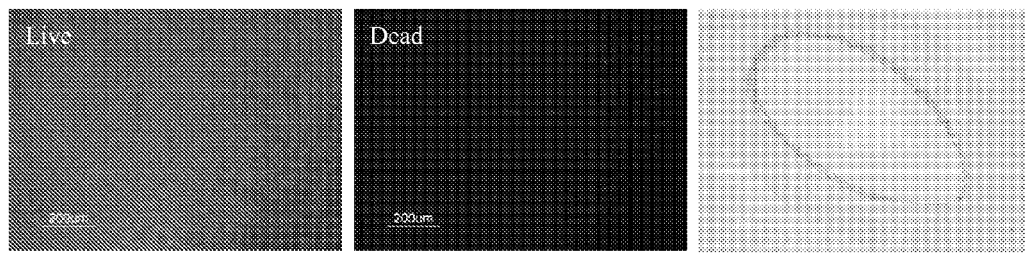

Individual tubular scaffolds were placed into 100 mm untreated plates (from Corning, Cat No 430591). Rat smooth muscle cells were seeded statically onto the tubular scaffolds coated with hUTC lysate or phosphate buffered saline (PBS) (as a control) at a seeding density of $5 \times 10^6$/scaffold. Cell seeded scaffolds were incubated in 37° C. humidified air for one hour prior to refeeding the dish with 15 milliliters smooth muscle growth media. The scaffolds were cultured for 24 hours. After 24 hours, the scaffolds were evaluated by Live/Dead kit (from Invitrogen, Cat No L3224). Live/Dead staining on tubular scaffolds coated with PBS or hUTC lysate and cultured with rat SMC for 24 hours showed more cell attached to the lysate-coated scaffold (FIG. 6).

Example 17

Generation of Cell Sheets on the Lysate Treated PDO Sheet

Figure 7:
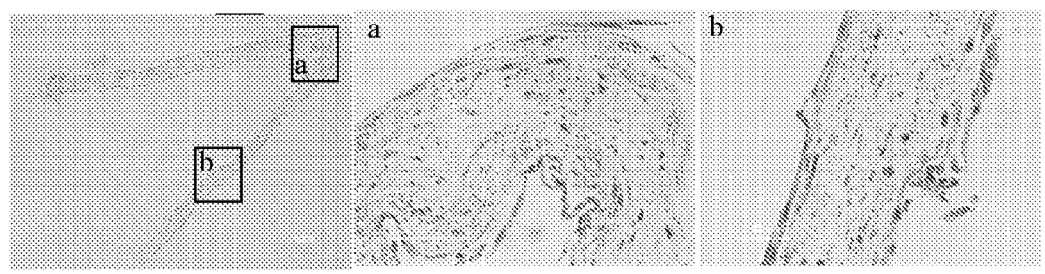

This example is to demonstrate hUTCs seeded on the lysate treated PDO sheet could attach, migrate and penetrate into the scaffold. These sheets could be fabricated into tubular structures leading to TEBV comprised solely of hUTC (see next example) for implantation right away at the site of injured vessel in vivo or further maturation by culturing in a bioreactor. A PDO sheet (2.0 cm×2.0 cm×0.01 μm) (Lot#3904-78) (Example 3) was soaked with 4 μl lysate (containing 5.2 mg/ml total protein, Lot#082908) followed by air drying at 4° C. for overnight. The treated scaffold was then seeded with hUTCs, cultured and obtained as described in Example 15, at a density of $1.75 \times 10^5$ cells/cm$^2$. The cell seeded scaffold was then cultured in the same condition as for cells described in Example 15. At 11 and 14 days after seeding, the cell sheets were fixed for H&E staining. As shown, while cells were seeded on only one side, cells spread all over the surface as well as inside the scaffold, indicating hUTCs attach, migrate and proliferate within the lysate treated PDO scaffold (FIG. 7).

Example 18

Tissue Engineered Graft of Rolled ESS Sheet with hUTC Cells and hUTC Cell Lysate Two PDO sheets (2×5×0.05 cm, Lot#5-6-08-2 sheet 3904-50-3) prepared as described in Example 3 were loaded with 700 μl PBS or hUTC lysate (containing 5.2 mg/ml total protein, Lot#082908 Low) and dried out by storing in −20° C. for 3 days. Each sheet was hydrated with 350 μl growth medium (15% FBS in DMEM). 350 μl hUTCs ($5 \times 10^6$ cells/ml) were obtained as described in Example 15 and loaded at a density $1.75 \times 10^5$/cm$^2$ (Cell lot#120304, P.9). The cell-loaded sheets were cultured in growth medium. At day 4, each sheet was cut into two (2×2.5×0.05 cm). One set was rolled to a single layer tube with 5 mm in diameter and 2.5 cm in length while the other set stayed in sheet format.

Figure 8:
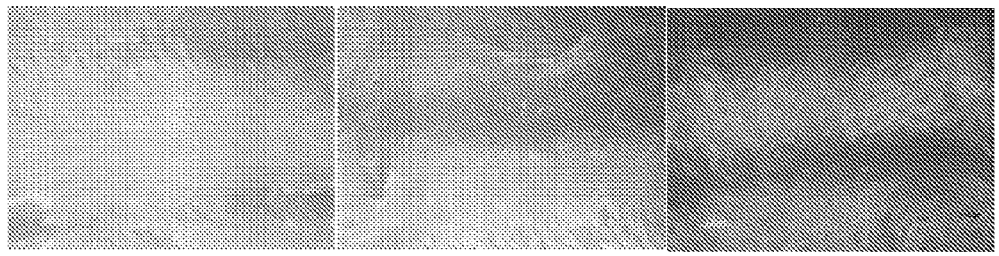
FIG. 8. The rolled tube cartoon shows the sampling areas for Live-Dead staining experiment. In a static culture, position 1c2 is the bottom of the tube, a and b are the side of the tube and 1d2 the top of the tube.
Figure 8:
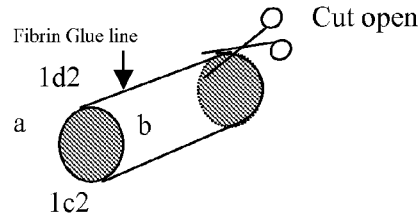
Figure 8:

Fibrin sealant (0.5 ml) (Omrix, Biopharmaceutices LTD, Tel Aviv Israel) was applied to the edge of rolled PDO ESS sheet followed by Thrombin (0.5 ml) (Omrix, Biopharmaceutices LTD, Tel Aviv Israel) to glue the end of the scaffold onto itself and keep the scaffold in a tube shape. The glued rolled tube was removed from the mandrel. A second sheet was kept as a sheet. All tubes and sheets were continued to culture at 37° C. The viability, attachment and proliferation of hUTCs in tubes and sheets were evaluated at 1 and 4 days after culture. The results showed that hUTC attached and grew to confluence on PDO sheet with or without lysate. Cell attachment is stronger with the lysate treated PDO sheet. While the cell layer formed on PDO sheet is disturbed during a rolling process since the cell density was low when evaluated on day 1 after the tube was formed, hUTC uniformly and densely distributed throughout the luminal surface of the tube, with more proliferation found for the PDO material treated with hUTC lysate (FIG. 8).

Example 19

Tissue Engineered Graft of Rolled ESS Sheet with rSMC Cells and hUTC Cell Lysate A PDO sheet (2×2.5×0.005 cm, lot#3904-72-23) as described in Example 3 was loaded with 601 hUTC lysate (containing 5.2 mg/ml total protein, lot#082908 Low). Approximately 250 μl rSMCs (Cell Applications, San Diego, Calif.) at $3.75 \times 10^6$ cells/ml were seeded on the PDO sheet at a density of $1.75 \times 10^5$ cells/cm². After 2 hrs at 37° C., the seeded material was immersed with SMC growth medium (GM). After 5 days in culture, the sheet was rolled to a tube (~4 layers) around a mandrel ($\phi$=2 mm).

A laboratory scale machine was fabricated to roll an ESS sheet into a graft that can be used to develop a tissue engineered blood vessel. The machine has a chuck to which a mandrel was connected that was rotated to allow the sheet to be rolled into a tube. A cell cultured PDO ESS sheet was placed on the mandrel (5 mm in diameter or 2 mm in diameter). The mandrel was slowly rotated to form 5 layers of a cell containing scaffold. The tube was sealed with fibrin sealant as described in example 17. The construct was cultured in GM for 5 days and switched to SMC Differentiation Medium (DM) for 4 more days. The construct was cut into 2 segments, one for Live-dead Staining and the other for H&E by fixing in 10% buffered formalin.

Figure 9:
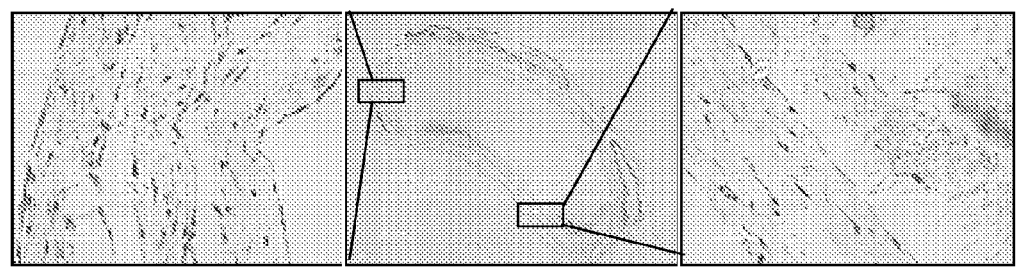
FIG. 9. H&E staining for the rolled PDO tube from an rSMC seeded sheet (50 micron in thickness).

The results show rSMC cells penetrate into the scaffold from both sides of the scaffold and attach and proliferate well within the scaffold throughout the thickness of the material. Some areas (right panel) show the integration of two layers (FIG. 9).

Example 20

Seeding of hUTC on 2 Mm Diameter Tissue-Engineered Blood Vessel Scaffolds

This example relates to the uniform seeding of human umbilical cord cells (hUTC) into PDO-ESS tubes of varying inner diameters, followed by culture to allow cell growth and matrix production. This growth can include static culture or culture under physiological conditions in a bioreactor, such as luminal flow with or without pressure and/or pulsatile flow. The PDO-ESS tubes can be first coated with type I collagen or other extracellular matrix component.

PDO-ESS tubes (100 mg/ml, Example 1, part 2) approximately 3.5 cm in length and 2 mm in inner diameter were coated with collagen by soaking in a solution of 50 micrograms/ml rat tail type I collagen (BD Biosciences, Bedford, Mass.). A collagen-coated tube and a non-coated control were secured to barbs within a LumeGen bioreactor chamber (Tissue Growth Technologies, Minnetonka Minn.) using silk sutures and the chambers were sealed. The outer chamber, which bathes the tubular scaffolds in medium, was filled with complete growth medium. hUTC were trypsinized, counted and resuspended to a concentration of $5.5 \times 10^5$ cells/ml in complete growth medium. Seeding rings were then attached to the LumeGen chamber. These rings allow for rotation of the chamber when placed on to a standard tissue culture bottle roller. The cell suspension was injected into the lumen of the PDO-ESS tubes using a syringe in a way that eliminated all air bubbles. The ends of the luminal chambers were sealed and the chambers were placed on the bottle roller and incubated overnight at 37° C. with a rotation of approximately 0.4 rpm. After this overnight incubation, the tubes were cut open and 5 mm biopsy punches taken to examine the distribution of cells within the TEBV scaffolds. The biopsies of the scaffolds were transferred to fresh low cluster 24-well dishes containing 1 ml PBS. A stock solution of Live/Dead stain containing 2 micromolar calcein AM and 4 micromolar ethidium homodimer was prepared and 0.5 ml was added separate wells. The scaffold punches were then transferred to the wells containing the Live/Dead solution. After incubation at room temperature for 5 minutes, cell attachment and viability of cells was assessed by fluorescence microscopy.

Figure 10:
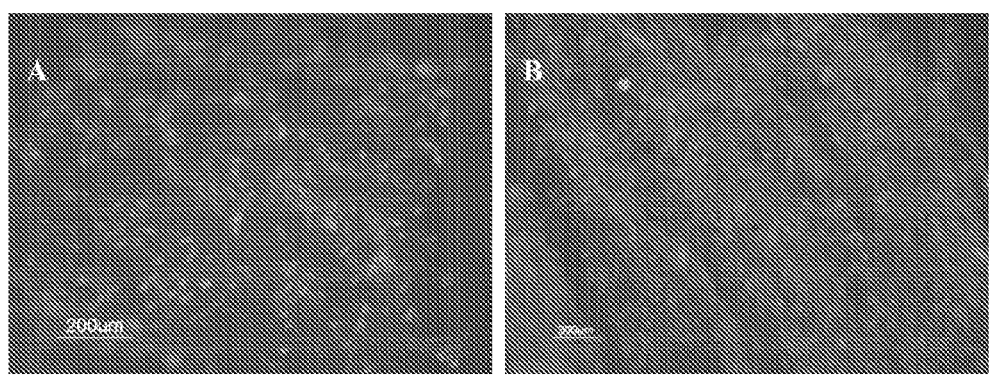
FIG. 10. Seeding of hUTC on 2 mm tubular scaffolds. PDO-ESS (A) and PDO-ESS coated with rat tail type I collagen (B) tubular scaffolds 2 mm in diameter were secured to LumeGen bioreactor chambers and seeded by filling the lumen with a cell suspension at $5.5\times10^5$ cells/ml. The chambers were then rotated at 0.4 rpm overnight and analyzed by Live/Dead staining. All images taken at 100× magnification.

Results:

Profuse cell attachment was observed for all PDO-ESS tubes seeded with hUTC. There was a dramatic increase in the number of cells attached to the collagen-coated PDO-ESS tube compared to the uncoated PDO-ESS tube. Very few dead cells were observed in either sample (FIG. 10).

Example 21

Bioreactor Processes for Tissue Engineered Blood Vessel Development (Static Culture)

This example related to the uniform seeding of smooth muscle cells into PDO-ESS tubes of varying inner diameters, followed by culture to allow cell growth and matrix production. This growth can include static culture or culture under physiological conditions in a bioreactor, such as luminal flow with or without pressure and/or pulsatile flow.

PDO-ESS tubes (100 mg/ml) or PDO/collagen-ESS tubes (Example 1, part 2 and Example 2, part 2) approximately 5 cm in length were secured to barbs within a LumeGen bioreactor chamber (Tissue Growth Technologies, Minnetonka Minn.) using silk sutures. After the chamber was sealed, the outer chamber which bathes the tubular scaffolds was filled with smooth muscle growth medium (Cell Applications, Inc., San Diego, Calif.). Rat aortic smooth muscle cells (Cell Applications, Inc.) were trypsinized, counted and resuspended to a concentration of $2 \times 10^6$ cells/ml in growth medium. Seeding rings were then attached to the LumeGen chamber. These rings allow for rotation of the chamber when placed on to a standard tissue culture bottle roller. The cell suspension was injected into the lumen of the PDO-ESS tube using a syringe. The ends of the luminal chamber were sealed and the chamber was placed on the bottle roller and incubated overnight at 37° C. with a rotation of approximately 0.4 rpm. After this overnight incubation, some tubes were cut open and 5 mm biopsy punches taken to examine the distribution of cells within the TEBV scaffolds. The biopsies of the scaffolds were transferred to fresh low cluster 24-well dishes containing 1 ml serum-free DMEM. The scaffolds were then washed with an additional 1 ml serum-free DMEM. A stock solution of Live/Dead stain containing 2 micromolar calcein AM and 4 micromolar ethidum homodimer was prepared and 0.5 ml was added to each well. After incubation at room temperature for 5 minutes, cell attachment and viability of cells was assessed by fluorescence microscopy.

Cell-seeded PDO-ESS scaffolds in the LumeGen chambers were then connected to the LumeGen bioreactor that is capable of generating physiological flow rate, pulsatile flows and pressures. The pulsatile flow comes partly from a peristaltic pump, while the pressure and pulses can be adjusted by crimping the outlet media flow tubing from either the lumen or chamber. In addition, pulses can optionally be added through a mechanism that compresses the graft in a pulsatile manner. This is controlled through a computer interface. Flow was initiated and the cells were exposed to a flow rate of 10 ml/min for 2 hours. After this flow period, one TEBV scaffold was removed form the chamber, and analyzed using Live/Dead stain as above. Another cell-seeded PDO-ESS scaffold was then cultured statically within the LumeGen chamber for 7 days followed by analysis with Live/Dead stain as above.

Figure 11:
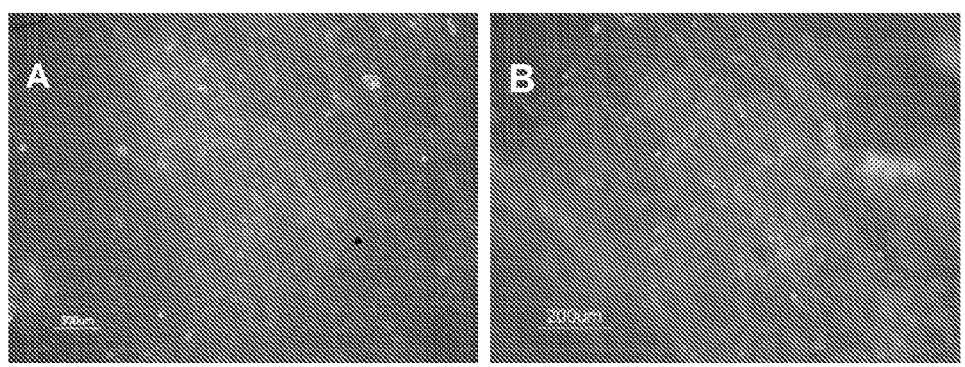
FIG. 11. Seeding of rat aortic smooth muscle cells on tubular scaffolds. PDO-ESS (A) and PDO/collagen-ESS (B) tubular scaffolds were secured to LumeGen bioreactor chambers and seeded by filling the lumen with a cell suspension at $2\times10^6$ cells/ml. The chambers were then rotated at 0.4 rpm overnight and analyzed by Live/Dead staining. All images taken at 100× magnification.
Figure 12:
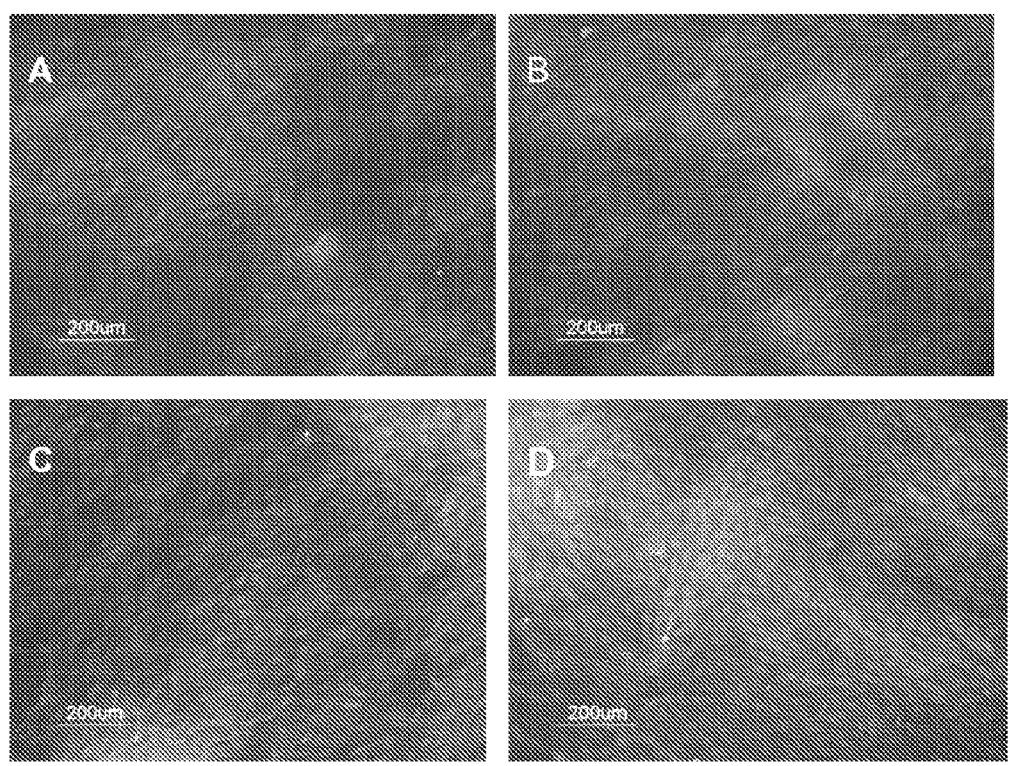
FIG. 12. Exposure of rat aortic smooth muscle cells on a tubular scaffold to fluid flow or 7 days of static culture. A PDO-ESS tubular scaffolds ~5 cm long were secured to LumeGen bioreactor chambers and seeded by filling the lumen with a cell suspension at $2\times10^6$ cells/ml. The chambers were then rotated at 0.4 rpm overnight. The next day, the tubular scaffolds were connected to the LumeGen bioreactor and exposed to flow at a rate of 10 ml/min for 2 hours. One tubular scaffold was then analyzed by Live/Dead staining. (A) Left side of the tube. (B) Right side of the tube. The other tubular scaffold was incubated statically for an additional 7 days then analyzed by Live/Dead staining. (C) Left side of the tube. (D) Right side of the tube. All images taken at 100× magnification.

Results:

The Live/Dead stain results show that the rotating seeding method within the LumeGen chamber enables cells to attach and spread on the PDO-ESS scaffolds with a homogeneous distribution of cells throughout the length of the scaffold (FIG. 11). Furthermore, the exposure of cells to 10 ml/min flow did not shear the cells form the luminal surface of the scaffold. Incubating the seeded scaffold for 7 days following flow resulted in an increase in cell number without affecting the viability of the cells (FIG. 12).

Example 22

Bioreactor Processes for Tissue Engineered Blood Vessel Development (Pulsatile Flow Physiological Conditions-Short Term Culture)

This example relates to the uniform seeding of smooth muscle cells into PDO-ESS tubes of varying inner diameters, followed by culture under dynamic conditions to allow cell growth and matrix production. These dynamic conditions can include culture under physiological or non-physiological conditions in a bioreactor, such as luminal flow with or without pressure and/or pulsatile flow. In addition, flow can be introduced to the outer chamber, which bathes the outside of the tissue engineered blood vessel construct in media.

PDO-ESS tubes (100 mg/ml, Example 1, part 2) approximately 5 cm in length and 4 mm in diameter were secured to barbs within a LumeGen bioreactor chamber (Tissue Growth Technologies, Minnetonka Minn.) using silk sutures and the chambers were sealed.

The outer chambers, which bathe the tubular scaffolds in medium, were filled with smooth muscle growth medium (Cell Applications, Inc). Rat aortic smooth muscle cells (Cell Applications, Inc.) were trypsinized, counted and resuspended to a concentration of $2\times10^6$ cells/ml in growth medium. Seeding rings were then attached to the LumeGen chamber. These rings allow for rotation of the chamber when placed on to a standard tissue culture bottle roller. The cell suspension was injected into the lumen of the PDO-ESS tube using a syringe. The ends of the luminal chamber were sealed and the chamber was placed on the bottle roller and incubated overnight at 37° C. with a rotation of approximately 0.4 rpm.

One cell-seeded PDO-ESS scaffold in the LumeGen chamber was then connected to the LumeGen bioreactor that is capable of generating physiological flow conditions, including pulsatile flows and pressures. The pulsatile flow comes partly from a peristaltic pump, while the pressure and pulses can be adjusted by crimping the outlet media flow tubing from either the lumen or chamber. In addition, pulses can be added through a mechanism that compresses the graft in a pulsatile manner. This is controlled through a computer interface. Flow was initiated and the cells seeded on the tubular scaffold were exposed to a flow rate of 20 ml/min and a pulsatile pressure of 120-80 mm Hg at a frequency of 1 Hz. As a control, another cell-seeded tube in the bioreactor chamber was cultured statically with a luminal media change after 24 hours.

After three days of culture, the tubular scaffolds were removed from the chambers, cut open, and 5 mm biopsy punches taken to examine the number, distribution, and morphology of cells within the TEBV scaffolds. The biopsy punches of the scaffolds were transferred to fresh low cluster 24-well dishes containing 1 ml PBS. A stock solution of Live/Dead stain containing 2 micromolar calcein AM and 4 micromolar ethidum homodimer was prepared and 0.5 ml was added to separate wells. The scaffold punches were then transferred to the wells containing the Live/Dead solution. After incubation at room temperature for 5 minutes, cell attachment and viability of cells was assessed by fluorescence microscopy.

Figure 13:
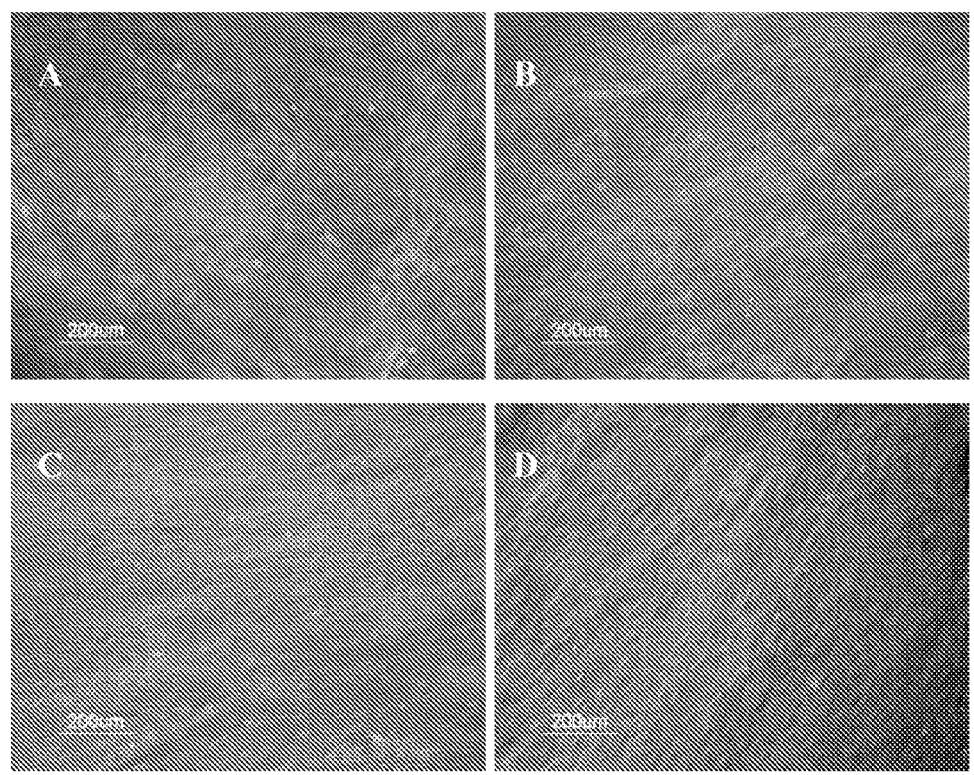
FIG. 13. Exposure of rat aortic smooth muscle cells on a tubular scaffold to dynamic or static culture conditions. PDO-ESS tubular scaffolds ~5 cm long were secured to LumeGen bioreactor chambers and seeded by filling the lumen with a cell suspension at $2\times10^6$ cells/ml. The chambers were then rotated at 0.4 rpm overnight. The next day, the tubular scaffolds were connected to the LumeGen bioreactor and exposed to flow at a rate of 20 ml/min and pulsatile pressure ranging from 120-80 mm Hg at a frequency of 1 Hz for 3 days. Another tubular scaffold was cultured under static conditions for the same time period. Both tubes were then analyzed by Live/Dead staining. (A) Left side of the tube cultured statically. (B) Right side of the tube cultured statically. (C) Left side of the tube cultured under dynamic conditions. (D) Right side of the tube cultured under dynamic conditions. All images taken at 100× magnification.

Results:

The Live/Dead stain results show that the rotating seeding method within the LumeGen chamber enables cells to attach and spread on the PDO-ESS scaffolds with a homogeneous distribution of cells throughout the length of the scaffold. Furthermore, the exposure of cells to 20 ml/min flow and physiological 120-80 mm Hg pulsatile pressure resulted in a dramatic increase in the number of cells on the surface of the scaffolds. In addition, the morphology of the cells was altered to align in the direction of the flow (FIG. 13).

Example 23

Bioreactor Processes for Cell Seeded Tissue Engineered Blood Vessel Development (Pulsatile Flow Physiological Conditions-Long Term Culture)

Cells (umbilical artery smooth muscle cells—UASMCs) are seeded on a scaffold as described in Examples 1-11 in a perfused rotating wall vessel bioreactor (Synthecon, Inc., Houston Tex.). The bioreactor has a central rotating core with barbs that the scaffolds will be connected to. The core allows for medium to be perfused through the lumen of the scaffold, while the exterior is bathed in medium. The entire assembly is rotated horizontally as above, again minimizing shear stress. For seeding of cells onto the luminal surface of the scaffolds, a cell suspension ($10^6$ cells/ml) is pumped into the lumen of the scaffold. The flow is stopped and rotation continues. As the bioreactor rotates, cells are attached to the surface of the rotating lumen in a uniform manner. After the 2 to 4 hour incubation period for attachment, the remaining unattached cells are flushed from the lumen, and growth medium perfused through the lumen. This culture period is continued for ~14 days, allowing the cells to grow and migrate into the pores of the scaffold (the actual time of culture will be determined empirically).

Growth of cells into the scaffolds will be examined by confocal microscopy following calcein staining and or actin staining using rhodamine-phalloidin. Similar techniques would be used to determine the depth of cell growth and/or migration into scaffold biomaterials. Cross-sectional images will be examined and the depth of cell ingrowth will be measured using image analysis tools.

Other cell-seeded scaffolds can be transferred to a second bioreactor (Tissue Growth Technologies, Inc.) that is capable of generating physiological flow rate, pulsatile flows and pressures. The pulsatile flow comes partly from a peristaltic pump, while the pressure and pulses can be adjusted by crimping the outlet media flow tubing from either the lumen or chamber. In addition, pulses can be added through a mechanism that compresses the graft in a pulsatile manner. This is controlled through a computer interface. The bioreactor has built-in pressure sensors, as well as a laser micrometer that measures the graft outer diameter. Flow rate, pressure and the graft outer diameter are graphed on the computer in real time. This allows the user to apply physiological pressures and pulsatile waves to a graft and to alter them in any way.

The cell-seeded grafts are cultured in this bioreactor for an additional period of time dependent on the desired physical and biological characteristics desired. During the first period of time, the pressure and flow rate are slowly increased to eventually reached the desired physiological levels. The final parameters depend on the eventual location of the scaffold. These levels are maintained during the final stages. For 1 hour each day, the following measurements will be recorded: pressure fluctuation within the bioreactor chamber; flow rate; and fluctuation in the outer diameter of the scaffold. At the end of the culture period, the pressure may be increased until graft failure to determine the burst-strength of construct.

Example 24

Bioreactor Processes for Cell Sheet Tissue Engineered Blood Vessel Development Cell sheets rolled into a tube as described in Examples 17-18 can be further bioprocessed to form a tissue engineered blood vessel using bioreactor processes. The cell sheets will be seeded with cells such as hUTCs or IMAs in a perfused rotating wall vessel bioreactor (Synthecon, Inc.). The bioreactor has a central rotating core with barbs that the scaffolds will be connected to. The core allows for medium to be perfused through the lumen of the scaffold, while the exterior is bathed in medium. The entire assembly is rotated horizontally as above, again minimizing shear stress. For seeding of cells onto the luminal surface of the cell sheets, a cell suspension ($10^6$ cells/ml) is pumped into the lumen of the tube. The flow is stopped and rotation continues. As the bioreactor rotates, cells are attach to the surface of the rotating lumen in a uniform manner. After the 2 to 4 hour incubation period for attachment, the remaining unattached cells are flushed from the lumen, and growth medium perfused through the lumen. This culture period is continued for ~14 days, allowing the cells to grow and migrate into the pores of the scaffold (the actual time of culture will be determined empirically).

Growth of cells into the scaffolds will be examined by confocal microscopy following calcein staining and or actin staining using rhodamine-phalloidin. Similar techniques would be used to determine the depth of cell growth and/or migration into scaffold biomaterials. Cross-sectional images will be examined and the depth of cell ingrowth will be measured using image analysis tools.

The cell-seeded scaffolds can be transferred to a second bioreactor (Tissue Growth Technologies, Inc.) that is capable of generating physiological flow rate, pulsatile flows and pressures. The pulsatile flow comes partly from a peristaltic pump, while the pressure and pulses can be adjusted by crimping the outlet media flow tubing from either the lumen or chamber. In addition, pulses can be added through a mechanism that compresses the graft in a pulsatile manner. This is controlled through a computer interface. The bioreactor has built-in pressure sensors, as well as a laser micrometer that measures the graft outer diameter. Flow rate, pressure and the graft outer diameter are graphed on the computer in real time. This allows the user to apply physiological pressures and pulsatile waves to a graft and to alter them in any way.

The cell-seeded grafts are cultured in this bioreactor for an additional period of time dependent on the desired physical and biological characteristics desired. During the first period of time, the pressure and flow rate are slowly increased to eventually reached the desired physiological levels. The final parameters depend on the eventual location of the scaffold. These levels are maintained during the final stages. For 1 hour each day, the following measurements will be recorded: pressure fluctuation within the bioreactor chamber; flow rate; and fluctuation in the outer diameter of the scaffold. At the end of the culture period, the pressure may be increased until graft failure to determine the burst-strength of construct.

Example 25

Preparation of Minced Tissue on Tubular Construct

Figure 14:
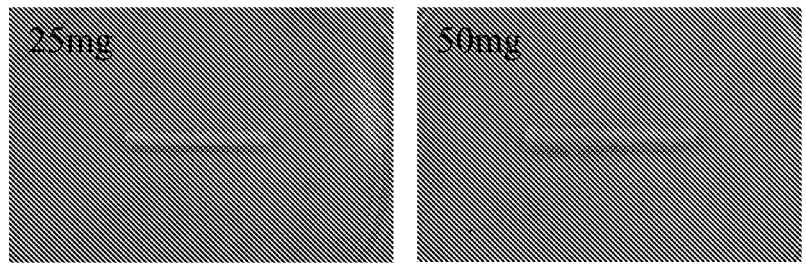
FIG. 14. Image showed minced rat muscle tissue were distributed uniformly over tubular constructs with different amount of tissue FIG. 15. After 72 hours culturing, image showed minced tissue still attached to the tubular scaffolds FIG. 16. Rat Smooth Muscle Cells seeded (static) on PDO tubes for 4 days followed by days in bioreactor (H&E staining)
Figure 15:
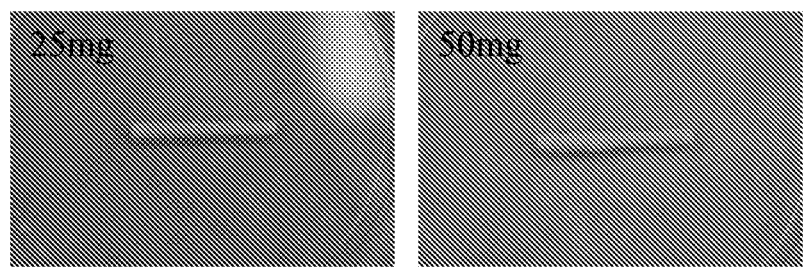

Two small biopsy tissues were harvested from rat muscle (Lewis rat from Harlan, Indianapolis, Ind.) by 5 mm diameter biopsy punch (Miltex, REF No 33-35). Each biopsy weighed around 50-60 mg and was placed in PBS supplemented with penicillin at standard concentrations (100 U/ml). The tissue was rinsed three times in PBS and minced into small pieces. Minced tissue was weighed and divided into 25 mg and 50 mg and then spread evenly on the outer surface of the each tubular construct (FIG. 14). The tissue fragments were held on the scaffold by using fibrin glue (EVICEL, Cat No 3905, Ethicon, Somerville, N.J.). The tubular construct was loaded with minced tissue and placed in an incubator at 37° C. for 2 hours and 72 hours (FIG. 15).

Example 26

Preparation of a Minced Tissue-Seeded TEBV Construct with Two Sources of Minced Tissue This example describes the preparation of a tissue-engineered blood vessel created from a bioabsorbable scaffold seeded with minced autologous tissue as the cell source. A tubular or flat bioresorbable scaffold with dimensions as outlined in Examples 1-11 is prepared. A small biopsy of tissue containing smooth muscle cells from tissue source e.g. muscle layers in the walls of hollow organs (such as the digestive tract, lower part of the esophagus, stomach and intestines, the walls of the bladder, the uterus, various ducts of glands and the walls of blood vessels) is obtained. The biopsied tissue is placed in PBS supplemented with penicillin at standard concentrations (100 U/ml). The tissue is rinsed three times in PBS and then minced with the help of scalpels to obtain minced tissue. The tissue is then distributed evenly on the outer surface of the tubular or flat construct. Another tissue biopsy is obtained from an endothelial tissue source for. e.g. the lining of the blood vessel. The tissue is placed in PBS supplemented with penicillin at standard concentrations (100 U/ml). The tissue is minced and distributed on the inner surface of the tubular construct or the inner surface of the flat construct. The tissue fragments in both cases can be held on the scaffold by using cell friendly glues for e.g. fibrin glue. Scaffold constructs that are flat can now be sutured into tubular constructs. The constructs can then be cultured in medium containing DMEM with Pen/Strep and 15% FBS for 4 to 8 weeks in low cell attachment dishes, during which smooth muscle cells and endothelial cells will migrate from the minced tissue on to the scaffolds. The engineered vessel can then be further cultured in a bioreactor for several weeks or months in an atmosphere of 10% $CO_2$ at a temperature of 37° C. in DMEM supplemented with 20% FBS, penicillin G (100 U/ml), 5 mM HEPES, ascorbic acid (0.05 mg/ml), $CuSO_4$ (3 ng/ml), proline (0.05 mg/ml), alanine (0.03 mg/ml), and glycine (0.05 mg/ml) as described in Example 27.

Example 27

Preparation of a Minced Tissue-Seeded TEBV Construct with a Single Source of Minced Tissue In another example, constructs seeded with minced tissue can be prepared as outlined in Example 25. The source of minced tissue can, however, be a single source such that the single tissue source contains both the smooth muscle cells and endothelial cells and the same minced tissue fragments are applied to the inner and outer surface of the scaffolds.

Example 28

Bioreactor Processes for Cell Lysate or Minced Tissue Engineered Blood Vessel Development Constructs containing minced tissue or cell lysate and scaffolds as described in Examples 1-11, 24-26 can be further bioprocessed to form a tissue engineered blood vessel using bioreactor processes. The constructs containing minced tissue and scaffolds will be seeded with cells such as hUTCs or IMAs in a perfused rotating wall vessel bioreactor (Synthecon Inc., Houston Tex.). The bioreactor has a central rotating core with barbs that the scaffolds will be connected to. The core allows for medium to be perfused through the lumen of the scaffold, while the exterior is bathed in medium. The entire assembly is rotated horizontally as above, again minimizing shear stress. For seeding of cells onto the luminal surface of the constructs containing minced tissue and scaffolds, a cell suspension ($10^6$ cells/ml) is pumped into the lumen of the construct. The flow is stopped and rotation continues. As the bioreactor rotates, cells are attach to the surface of the rotating lumen in a uniform manner. After the 2 to 4 hour incubation period for attachment, the remaining unattached cells are flushed from the lumen, and growth medium perfused through the lumen. This culture period is continued for ~14 days, allowing the cells to grow and migrate into the pores of the scaffold (the actual time of culture will be determined empirically).

Growth of cells into the scaffolds will be examined by confocal microscopy following calcein staining and or actin staining using rhodamine-phalloidin. Similar techniques would be used to determine the depth of cell growth and/or migration into scaffold biomaterials. Cross-sectional images will be examined and the depth of cell ingrowth will be measured using image analysis tools.

The cell-seeded scaffolds can be transferred to a second bioreactor (Tissue Growth Technologies, Inc.) that is capable of generating physiological flow rate, pulsatile flows and pressures. The pulsatile flow comes partly from a peristaltic pump, while the pressure and pulses can be adjusted by crimping the outlet media flow tubing from either the lumen or chamber. In addition, pulses can be added through a mechanism that compresses the graft in a pulsatile manner. This is controlled through a computer interface. The bioreactor has built-in pressure sensors, as well as a laser micrometer that measures the graft outer diameter. Flow rate, pressure and the graft outer diameter are graphed on the computer in real time. This allows the user to apply physiological pressures and pulsatile waves to a graft and to alter them in any way.

The cell-seeded grafts are cultured in this bioreactor for an additional 7 days. During the first 3 days, the pressure and flow rate are slowly increased to eventually reached the desired physiological levels. The final parameters depend on the eventual location of the scaffold. These levels are maintained for the final 4 days. For 1 hour each day, the following measurements will be recorded: pressure fluctuation within the bioreactor chamber; flow rate; and fluctuation in the outer diameter of the scaffold. At the end of the culture period, the pressure may be increased until graft failure to determine the burst-strength of construct.

Example 29

In-Vivo Efficacy Study of TEBV

TEBVs are surgically implanted in the femoral arteries of 14 adult dogs. 5 to 10 mm sections of the native vessel are removed and replaced with the experimental TEBV using standard surgical techniques. Anastomoses are performed using standard suture techniques. The vessel lumen are irrigated with a standard heparin solution. The muscle and skin are closed by standard techniques. Postoperatively, the patency is monitored by standard Ultrasound.

The TEBVs are explanted after 4 weeks and the patency is assessed by direct inspection. Patency is confirmed by excising the TEBV and evaluating the lumen histologically.

Example 30

Use of TEBV in the Treatment of Coronary Heart Disease Patient

In a coronary by-pass (CABG) procedure, a TEBV would be used for patients suffering from arteriosclerosis, a common arterial disorder characterized by arterial walls that have thickened (blockages), have lost elasticity, and have calcified. This leads to a decrease in blood supply which can lead to damage to the heart, stroke and heart attacks.

Thus, a PDO tubular scaffold fabricated by electrospinning processes described in Example 1 and then cell seeded and bioreactor processed as described in Example 10, forms a TEBV that is then sterilized, packaged and delivered to an operating room. In a typical CABG procedure, the surgeon opens the chest via a sternotomy. The heart's functions are taken over by a Heart and Lung machine. The diseased artery is located and one end of the TEBV is sewn onto the coronary arteries beyond the blockages and the other end is attached to the aorta. The heart is restarted, the sternum is wired together and the incisions are sutured closed. Within a few weeks, the successful by-pass procedure is fully healed and the patient is functioning normally.

The above description is merely illustrative and should not be construed to capture all consideration in decisions regarding the optimization of the design and material orientation. Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular embodiments described and illustrated, but should be constructed to cohere with all modifications that may fall within the scope for the appended claims.

Example 31

Mammary Artery Derived Cells: Isolation and Characterization

Mammary Artery Derived Cell Isolation

Internal mammary artery (IMA) will be obtained from the National Disease Research Interchange (NDRI, Philadelphia, Pa.). To remove blood and debris, the artery will be trimmed and washed in Dulbecco's modified Eagles medium (DMEM-low glucose; Invitrogen, Carlsbad, Calif.) or phosphate buffered saline (PBS; Invitrogen). The artery will then be mechanically dissociated in tissue culture plates until the tissue is minced to a fine pulp. The tissue will then be transferred to a 50-milliliter conical tube. The tissue will then be digested in an enzyme mixture containing 0.25 Units/milliliter collagenase (Serva Electrophoresis, Heidelberg, Germany), 2.5 Units/milliliter dispase (Roche Diagnostics Corporation, Indianapolis Ind.) and 1 Units/milliliter hyaluronidase (Vitrase, ISTA Pharmaceuticals, Irvine, Calif.). The enzyme mixture will then be combined with growth medium (DMEM-low glucose (Gibco), penicillin (50 Units/milliliter) and streptomycin (50 ug/mL, Gibco)) containing 1% fetal bovine serum (FBS). The conical tube containing the tissue, medium and digestion enzymes will be incubated at 37° C. in an orbital shaker at 225 rpm for 2 hours.

The digest is centrifuged at 150×g for 5 minutes, the supernatant will then be aspirated. The pellet will then be resuspended in 20 milliliters of medium. The cell suspension will then be filtered through a 40-micron nylon BD FALCON Cell strainer (BD Biosciences, San Jose, Calif.). The filtrate will then be resuspended in medium (total volume 50 milliliters) and centrifuged at 150×g for 5 minutes. The supernatant will then be aspirated and the cells will be resuspended in another 50 milliliters of fresh culture medium. This washing procedure will be repeated twice more.

After the final centrifugation, cells will be plated in growth medium containing either 1% FBS or 10% FBS and cultured at 37° C. and 5% CO2). Fragments of IMA will also be cultured as explants in coated or non-coated tissue culture flasks. Cells that migrate out of the tissue fragments, under media selection, will be harvested using trypsin or other non-enzymatic methods.

For karyotype analysis, passage 4 and passage 10 mammary artery derived cells will be plated into T25 flasks and allowed to attach overnight. Flasks will then be filled with REGM and sent to the University of Medicine and Dentistry of New Jersey for karyotype analysis.

Analysis of Growth Potential

IMA derived cells will be plated at 5000 cells/cm$^2$ onto T75 flasks in growth medium and cultured at 37° C. in 5% carbon dioxide. Cells will be passaged every 3-5 days. At each passage, cells are counted and viability is measured using a Guava instrument (Guava Technologies, Hayward, Calif.). Population doublings [ln(final cell yield/initial number of cells plated)/ln 2] are then calculated.

Flow Cytometry

Flow cytometry analysis will be performed on IMA derived cells. Cells will be expanded to passage four and ten in growth medium on T225 flasks at 37° C. and 5% carbon dioxide. Adherent cells will be washed in PBS and detached with Trypsin/EDTA (Gibco). Cells will be harvested, centrifuged and resuspended in 3% (v/v) FBS in PBS at a concentration of 1×10$^7$ cells/mL. The specific antibody will be added to 100 microliters of cell suspension and the mixture is incubated in the dark for 30-45 minutes at 4° C. After incubation, cells will be washed with PBS and centrifuged to remove excess antibody. Cells will be resuspended in 500 microliters PBS and analyzed by flow cytometry. Flow cytometry analysis will be performed with a Guava instrument. Antibodies to be used are shown in Table 3.

TABLE 3

Antibodies to be used in characterizing cell surface markers of IMA derived cells.

| Antibody | Manufacture | Catalog number |
|---|---|---|
| CD34 | BD Pharmingen | 555821 |
| CD44 | BD Pharmingen | 555478 |
| CD45R | BD Pharmingen | 555489 |
| CD117 | BD Pharmingen | 340529 |
| CD141 | BD Pharmingen | 559781 |
| CD31 | BD Pharmingen | 555446 |
| CD133 | Miltenyi Biotech | 120-001-243 |
| SSEA4 | R&D Systems | FAB1435P |
| CD105 | SantaCruz Biotech | SC-21787 |
| CD104 | BD Pharmingen | 555720 |
| CD166 | BD Pharmingen | 559263 |
| CD29 | BD Pharmingen | 555442 |
| IgG-FITC | BD Pharmingen | 555748 |
| IgG-PE | BD Pharmingen | 555749 |

Total RNA Isolation

RNA will be extracted from IMA derived cells. (RNeasy Mini Kit; Qiagen, Valencia, Calif.). RNA will be eluted with 50 μL DEPC-treated water and stored at −80° C.

Reverse Transcription

RNA will be reversed transcribed using random hexamers with the TaqMan reverse transcription reagents (Applied Biosystems, Foster City, Calif.) at 25° C. for 10 minutes, 37° C. for 60 minutes and 95° C. for 10 minutes. Samples will be stored at −20° C. Selected genes (see table below) will be investigated using conventional PCR.

PCR

PCR reactions (with the exception of GAPDH—see chart below) will be performed on cDNA samples using RT$^2$ PCR Primer sets (SuperArray Biosciences Corp, Frederick Md.). All primers shown below will be sequence verified.

| GENE | CATALOG NUMBER |
|---|---|
| Oct 4 | PPH02394A |
| Rex 1 | PPH02395A |
| Sox2 | PPH02471A |
| Human TERT (hTERT) | PPH00995A |
| FGF4 | PPH00356A |

Primers will be mixed with 1 μL of cDNA and 2× ReactionReady™ SYBR Green PCR Master Mix (SuperArray Biosciences) according to manufacturer's instructions and PCR will be performed using an ABI Prism 7000 system (Applied Biosystems, Foster City, Calif.). Thermal cycle conditions will be initially 50° C. for 2 min and 95° C. for 10 min followed by 34 cycles of 95° C. for 15 sec and 60° C. for 1 min. For GAPDH, PCR will be performed using GAPDH primers from Applied Biosystems (cat#: 402869) 1 μL of cDNA solution and 1× AmpliTaq Gold universal mix PCR reaction buffer (Applied Biosystems, Foster City, Calif.) according to manufacturer's protocol. Primer concentration in the final PCR reaction will be 0.5 μM for both the forward and reverse primer and the TaqMan probe is not added. Samples will be run on 2% (w/v) agarose gel and stained with ethidium bromide (Sigma, St. Louis, Mo.). Images will be captured using a 667 Universal Twinpack film (VWR International, South Plainfield, N.J.) using a focal-length Polaroid™ camera (VWR International, South Plainfield, N.J.).

ELISA

IMA derived cells will be thawed at passage four and passage ten and seeded onto T75 flasks at 5000 cells/cm$^2$ each containing 15 milliliters of growth medium. Cells will be cultured for 24 hours at 37° C. in 5% carbon dioxide and atmospheric oxygen. The medium will be changed to a serum-free medium (DMEM-low glucose (Gibco), 0.1% (w/v) bovine serum albumin (Sigma), penicillin (50 Units/milliliter) and streptomycin (50 ug/mL, Gibco)) and further cultured for 8 hours. Conditioned, serum-free medium is then collected at the end of incubation by centrifugation at 14,000×g for 5 min and stored at −20° C.

To estimate the number of cells in each flask, cells will be washed with PBS, detached using 2 milliliters trypsin/EDTA (Gibco) and counted with a Guava instrument (Guava Technologies Hayward, Calif.). Samples are then assayed for the following factors: tissue inhibitor of metalloproteinase-1 (TIMP1), tissue inhibitor of metalloproteinase-2 (TIMP2), platelet-derived epithelial growth factor bb (PDGFbb), keratinocyte growth factor (KGF), hepatocyte growth factor (HGF), fibroblast growth factor (FGF), vascular endothelial growth factor (VEGF), Heparin-binding epidermal growth factor (HB-EGF), monocyte chemotactic protein-1 (MCP1), interleukin-6 (IL6), interleukin-8 (IL8), transforming growth factor alpha (TGFa), brain-derived neurotrophic factor (BDNF), stromal-derived factor 1B (SDF1B), cilliary neurotrophic factor (CNTF), basic nerve growth factor (bNGF), neurotrophin-3 (NT3) with the Searchlight Proteome Arrays (Pierce Biotechnology Inc.).

Example 32

Seeding of Rat Smooth Muscle Cells R354-05 into PDO Scaffolds

This example relates to the uniform static seeding of rat smooth muscle cells R354-05 (Cell Applications) into PDO-ESS tube (Example 1, part 2). Cells are cultured to allow cell growth and matrix production. This growth can include static culture or culture under physiological conditions in a bioreactor, such as luminal flow with or without pressure and/or pulsatile flow.

PDO tubes were cut in 2 cm length and placed in a 60 mm tissue culture dish. Rat aortic smooth muscle cells (Cell Applications, Inc.) were trypsinized, counted and resuspended in rat smooth muscle growth medium at a concentration of $2 \times 10^6$ cells/ml. Using a 200 ul pipet tip cells were gently dripped onto the PDO tube. The PDO tubes containing the cells were left at room temperature for one hour before being placed in a 37° C. humidified environment for 4 days.

Figure 16:
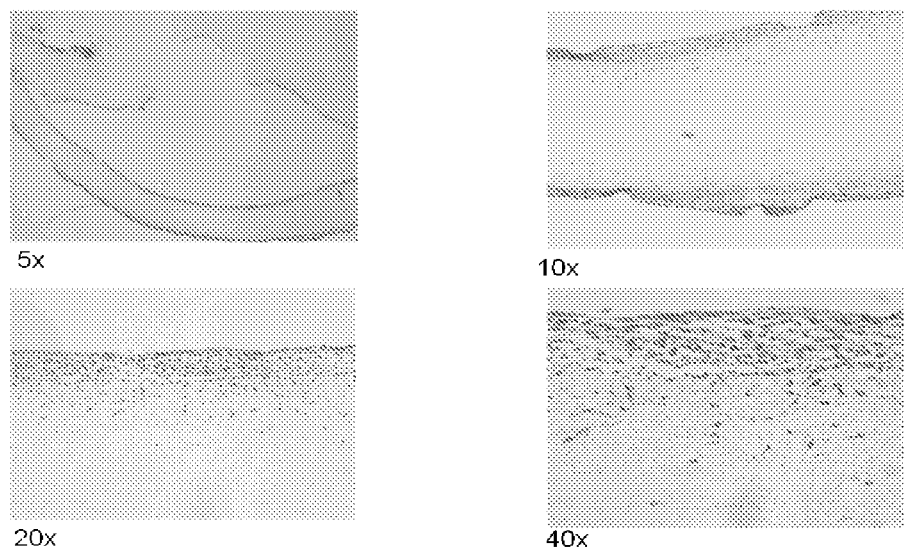

After four days of static culture PDO tubes were placed in a rotary cell culture system (Synthecon) for ten days at 7.0 rpm to allow cell growth and matrix product. At 14 days in culture, the distribution and morphology of the cells is evaluated. PDO tubes were transferred to a 60 mm tissue culture dish. 5 mm biopsy punches were harvested and placed in a 24 well plate containing PBS. To test the viability of the cells, a live/dead assay (Molecular Probes) was performed. Ten mls of PBS containing 2 micromolar calcein AM and 4 micromolar ethidum homodimer were prepared. One ml of the live/dead stain was added to the biopsies. After incubation at room temperature for 5 minutes, cell attachment and viability of cells was assessed by fluorescence microscopy. Similar punch biopsies were fixed in 10% neutral buffered formalin, embedded in paraffin, sectioned and stained with H&E to evaluate cell morphology (FIG. 16) and Masson's Trichome stain which is specific for the formation of extracellular matrix.

Results:

Rat smooth muscle cells are viable throughout the culture period with the PDO tubes supporting cell viability. Static seeding of the rat smooth muscle cells for four days leads to an even cell distribution. Cells attach on both sides of the scaffolds. Cell infiltration into the scaffolds is observed.

We claim:

1. A method of making a tissue engineered blood vessel comprising the steps of:
    a. Providing a scaffold comprising a solution of poly(p-dioxanone) and 1,1,1,3,3,3-hexafluoro-2-propanol solvent formed as an electrospun tubular scaffold of randomly oriented fibers;
    b. Cutting the electrospun tubular scaffold to form a scaffold sheet;
    c. Seeding said scaffold sheet with cells;
    d. Rolling said seeded sheet into a tube; and
    e. Culturing the tube in a bioreactor.

* * * * *